United States Patent
Nichols et al.

(10) Patent No.: US 8,221,697 B2
(45) Date of Patent: Jul. 17, 2012

(54) APPARATUS FOR LIDDING OR DELIDDING MICROPLATE

(76) Inventors: Michael J. Nichols, Boston, MA (US);
Louis J. Guarracina, Newburyport, MA (US)

(*) Notice: Subject to any disclaimer, the term of this patent is extended or adjusted under 35 U.S.C. 154(b) by 100 days.

(21) Appl. No.: 12/848,674

(22) Filed: Aug. 2, 2010

(65) Prior Publication Data

US 2011/0293488 A1   Dec. 1, 2011

Related U.S. Application Data

(63) Continuation-in-part of application No. 12/008,829, filed on Jan. 14, 2008, now Pat. No. 7,767,154.

(60) Provisional application No. 60/880,173, filed on Jan. 12, 2007.

(51) Int. Cl.
*B01L 3/00* (2006.01)

(52) U.S. Cl. ............ 422/400; 422/63; 422/534; 422/65; 422/527; 422/537; 29/559; 29/283; 29/407.04; 269/303; 269/309; 269/318; 435/287.2; 435/6.14; 436/37

(58) Field of Classification Search ....................... 29/559
See application file for complete search history.

(56) References Cited

U.S. PATENT DOCUMENTS

| | | | |
|---|---|---|---|
| 747,181 | A | 12/1903 | Jackson et al. |
| 4,040,234 | A | 8/1977 | Stockdale et al. |
| 4,482,182 | A | 11/1984 | Mortensen |
| 4,963,493 | A | 10/1990 | Daftsios |
| 5,342,581 | A | 8/1994 | Sanadi |
| 5,516,490 | A | 5/1996 | Sanadi |
| 5,587,321 | A | 12/1996 | Smith et al. |
| 5,741,463 | A | 4/1998 | Sanadi |
| 5,842,573 | A | 12/1998 | Halvorsen |
| 5,854,065 | A | 12/1998 | Livingston et al. |
| 5,910,287 | A | 6/1999 | Cassin et al. |
| 6,021,917 | A | 2/2000 | Lovell et al. |
| 6,054,100 | A | 4/2000 | Stanchfield et al. |
| 6,171,780 | B1 | 1/2001 | Pham et al. |
| 6,254,833 | B1 | 7/2001 | Shumate et al. |
| 6,258,325 | B1 | 7/2001 | Sanadi |

(Continued)

FOREIGN PATENT DOCUMENTS

DE   20219127   6/2003

(Continued)

OTHER PUBLICATIONS

Smith-Hewitt, European Application No. 11159117.8-2113, Extended European Search Report, dated Nov. 3, 2011, 7 pages.

(Continued)

*Primary Examiner* — Sally Merkling
(74) *Attorney, Agent, or Firm* — Hoffman Warnick LLC

(57) ABSTRACT

An automated lidder and/or delidder apparatus to engage and disengage a lid from a microplate is disclosed. The microplate includes a sample area with a plurality of individual wells and a hollow outer frame formed around the sample area, the frame being shaped to include a plurality of openings in its top surface. The lid includes a plate and a plurality of latches formed on the underside of the plate. In the lidding process, the apparatus presses down on the lid to insert each latch through a corresponding opening in the microplate until the latch snaps into engagement with the frame. In the delidding process, the apparatus inserts delidding posts into the openings to disengage the latches from the frame.

12 Claims, 36 Drawing Sheets

U.S. PATENT DOCUMENTS

| | | | |
|---|---|---|---|
| 6,426,050 B1 | 7/2002 | Pham et al. | |
| 6,426,215 B1 | 7/2002 | Sandell | |
| 6,436,351 B1 | 8/2002 | Gubernator et al. | |
| 6,449,827 B1 * | 9/2002 | Clarke et al. | 29/559 |
| 6,486,401 B1 | 11/2002 | Warhurst et al. | |
| 6,534,014 B1 | 3/2003 | Mainquist et al. | |
| 6,543,203 B2 | 4/2003 | Thompson et al. | |
| 6,602,704 B1 | 8/2003 | Maxwell et al. | |
| 6,669,911 B1 | 12/2003 | Swanson | |
| 6,716,350 B2 | 4/2004 | Olivier et al. | |
| 6,825,042 B1 | 11/2004 | Shumate et al. | |
| 6,861,035 B2 | 3/2005 | Pham et al. | |
| 6,896,848 B1 | 5/2005 | Warhurst et al. | |
| 6,918,738 B2 | 7/2005 | Lafferty et al. | |
| 6,939,516 B2 | 9/2005 | Hall et al. | |
| 2003/0235519 A1 * | 12/2003 | Sha et al. | 422/102 |
| 2005/0019225 A1 | 1/2005 | Sanadi | |
| 2007/0020152 A1 | 1/2007 | Costello et al. | |
| 2007/0172395 A1 | 7/2007 | Lim et al. | |
| 2007/0258864 A1 | 11/2007 | Braymer et al. | |

FOREIGN PATENT DOCUMENTS

| | | |
|---|---|---|
| EP | 1333286 | 6/2003 |
| EP | 1630560 A1 | 1/2006 |
| WO | 0025922 | 5/2000 |
| WO | 2007138085 A2 | 12/2007 |
| WO | 2008088781 A1 | 7/2008 |

OTHER PUBLICATIONS

Patent Cooperation Treaty (PCT) Search Report, International App. No. PCT/US 08/00468, May 21, 2008, 7 pages.

European Search Report, App. No. 08713116.5-2113/2125214, Jun. 10, 2010, 6 pages.

U.S. Appl. No. 12/008,829, Notice of Allowance and Fees Due, Jun. 29, 2010, 9 pages.

U.S. Appl. No. 12/008,829, Final Office Action Communication, Dec. 21, 2009, 11 pages.

U.S. Appl. No. 12/008,829, Office Action Communication, Jun. 2, 2009, 19 pages.

Warden, International Application No. PCT/US08/00468, International Preliminary Examination Report, dated Jun. 10, 2009, 9 pages.

* cited by examiner

APPARATUS FOR LIDDING OR DELIDDING MICROPLATE

CROSS-REFERENCE TO RELATED APPLICATIONS

The present application is a continuation-in-part of U.S. application Ser. No. 12/008,829, filed Jan. 14, 2008, now U.S. Pat. No. 7,767154, which claims the benefit under 35 U.S.C. 119(e) of U.S. Provisional Patent Application Ser. No. 60/880,173, filed on Jan. 12, 2007, both of which are incorporated by reference herein.

BACKGROUND OF THE INVENTION

The present invention relates generally to microplates that are typically used in the life sciences industry and more particularly to an apparatus for lidding and/or delidding microplates.

In the areas of biological, chemical and pharmaceutical research, it is a common practice to utilize microplates for storage and analytical purposes. Microplates (also commonly referred to in the art as multi-well plates, specimen plates and microtitre plates) have a block-shaped design and include a plurality of wells (e.g., 1, 2, 4, 6, 12, 24, 48, 96, 384, 1536, etc.) in its top surface, each well serving as an individualized receptacle for retaining a particular specimen.

It is well known in the art to seal the top surface of conventional microplates in order to, among other things, minimize the risk of contamination, degradation, moisture absorption and/or evaporation of specimens retained within each well. Presently, there are a number of different means for sealing conventional microplates.

As an example, it is well known for a foil seal to be affixed to the top surface of a microplate using a thermally activated adhesive. In order to access a particular well in the microplate after the foil seal has been applied (e.g., to retrieve a specimen retained therein), a laboratory technician either manually removes (i.e., peels off) at least a portion of the foil seal or punctures the portion of the foil that directly covers the particular well using a separate seal-piercing instrument.

Although widely used in the art, the use of a foil seal to enclose a microplate introduces a number of notable shortcomings. As a first shortcoming, it has been found to be rather difficult to adhere a secondary foil layer on a microplate after the primary foil layer has been removed or pierced, thereby precluding reuse of the microplate, which is highly undesirable. As a second shortcoming, it has been found to be rather difficult to determine the exact location of an individual well in a high density microplate (e.g., microplates with at least 1536 wells) through the foil seal. Accordingly, prior to locating the selected well using the foil piercing instrument, a laboratory technician often accidentally pierces the portion of the foil seal which directly covers one or more neighboring wells, which is highly undesirable.

As another example, in U.S. Pat. No. 6,534,014 to J. K. Mainquist et al, which is hereby incorporated by reference, there is disclosed a specimen plate lid that includes a sealing perimeter. In use, the lid is weighted so that when positioned on the specimen plate, the considerable weight of the lid compresses the seal against the sealing surface on the specimen plate.

Although known in the art, the lid described in the '014 patent suffers from two notable shortcomings. As a first shortcoming, the considerable weight associated with such a lid renders it difficult to use with most robots used in the life sciences market for picking and placing microtitre plates. As a second shortcoming, the footprint of such a lid is typically larger than the industry standard, thereby precluding its use with standard industry stackers, carousels and incubators.

As another example, in U.S. Pat. No. 6,939,516 to J. P. Hall et al., which is incorporated herein by reference, there is disclosed a multi-well plate cover that includes a lid and a gasket. The lid is formed of a resilient material and configured to apply a compressive spring force to the surface of the gasket to seal the wells in a multi-well plate when the cover is secured to the multi-well plate. The lid has members for mechanical manipulation and for attachment to the multi-well plate.

Although known in the art, the lid described in the '516 patent suffers from a notable shortcoming. Specifically, the lid described in the '516 patent is mechanically complex in nature. As a result, such a lid requires complicated and expensive machinery to assist in its sealing/removal through automated means, which is highly undesirable.

Other patents of interest include U.S. Pat. No. 6,254,833 to C. Shumate et al., and U.S. Pat. No. 6,543,203 to S. Thompson et al., both of these references being incorporated herein by reference.

SUMMARY OF THE INVENTION

An automated lidder and/or delidder apparatus to engage and disengage a lid from a microplate is disclosed. The microplate includes a sample area with a plurality of individual wells and a hollow outer frame formed around the sample area, the frame being shaped to include a plurality of openings in its top surface. The lid includes a plate and a plurality of latches formed on the underside of the plate. In the lidding process, the apparatus presses down on the lid to insert each latch through a corresponding opening in the microplate until the latch snaps into engagement with the frame. In the delidding process, the apparatus inserts delidding posts into the openings to disengage the latches from the frame.

A first aspect of the invention provides an apparatus for lidding or delidding a microplate, the apparatus comprising: a platform configured to hold a microplate, wherein the microplate comprises a sample area shaped to define a plurality of individual wells, and includes at least one opening; a lidding assembly positioned above the platform, the lidding assembly including a coupling device configured to couple the lidding assembly to a lid for the microplate, wherein the lidding assembly is configured to move the lid between a first position proximate to the microplate and a second position away from the microplate, wherein the lid includes at least one projection projecting substantially orthogonally towards the microplate, each projection dimensioned to project at least partially through a corresponding opening in the microplate in response to the lid being mounted on the microplate in the first position; and a base positioned below the platform, the base having at least one delidding post projecting substantially orthogonally towards the microplate, wherein the base is configured to move between a third position proximate to the microplate and a fourth position away from the microplate, wherein each delidding post is configured to extend into a corresponding opening in the microplate to engage and release a corresponding projection from the microplate in response to the base being in the third position.

Various other features and advantages will appear from the description to follow. In the description, reference is made to the accompanying drawings which form a part thereof, and in which is shown by way of illustration, an embodiment for practicing the invention. The embodiment will be described in sufficient detail to enable those skilled in the art to practice the invention, and it is to be understood that other embodiments may be utilized and that structural changes may be made without departing from the scope of the invention. The following detailed description is therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the present invention and, together with the description, serve to explain the principles of the invention. In the drawings, wherein like reference numerals represent like parts.

DETAILED DESCRIPTION OF THE INVENTION

Figure 1:
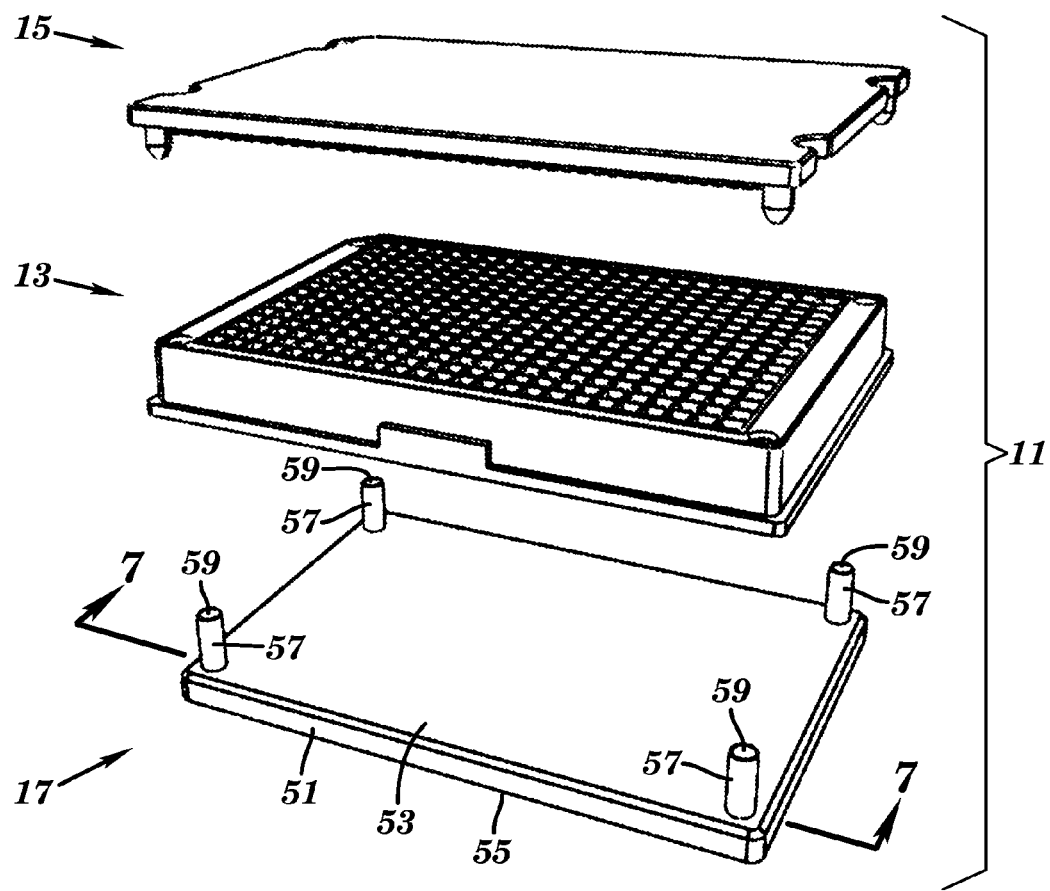
FIG. 1 is an exploded, top perspective view of a first embodiment of a microplate kit constructed according to the teachings of the present invention.

Referring now to FIG. 1, there is shown an exploded, top perspective view of a first embodiment of a microplate kit that is constructed according to the teachings of the present invention and identified generally by reference numeral 11.

Microplate kit 11 comprises a microplate 13, a lid 15 and a lid removal tool 17. As will be described in detail below, lid 15 is designed to be mounted on microplate 13. Tool 17 is designed to assist in the removal (i.e., or delidding) of lid 15 when mounted on microplate 13.

Figure 2:
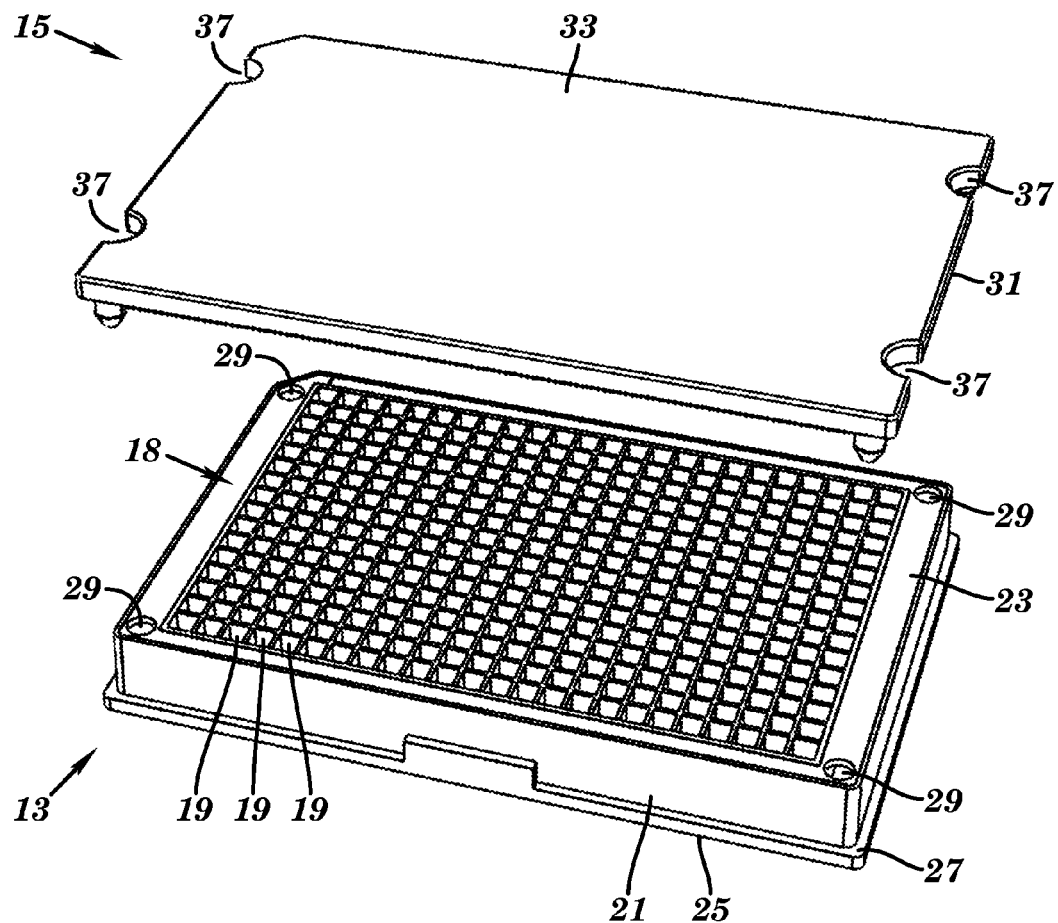
FIG. 2 is an exploded, top perspective view of the microplate and lid shown in FIG. 1.

Referring now to FIG. 2, microplate 13 has a generally block-shaped design and includes an enlarged sample area 18 that is provided with a plurality of individual, vertically-disposed wells 19. In the present embodiment, microplate 13 is represented as having 384 wells. However, it is to be understood that the present invention is not limited to any particular density of wells 19. Rather, the number of wells 19 could be modified to any density without departing from the spirit of the present invention (e.g., 96, 1536 or even greater than 1536 wells).

Figure 5A:
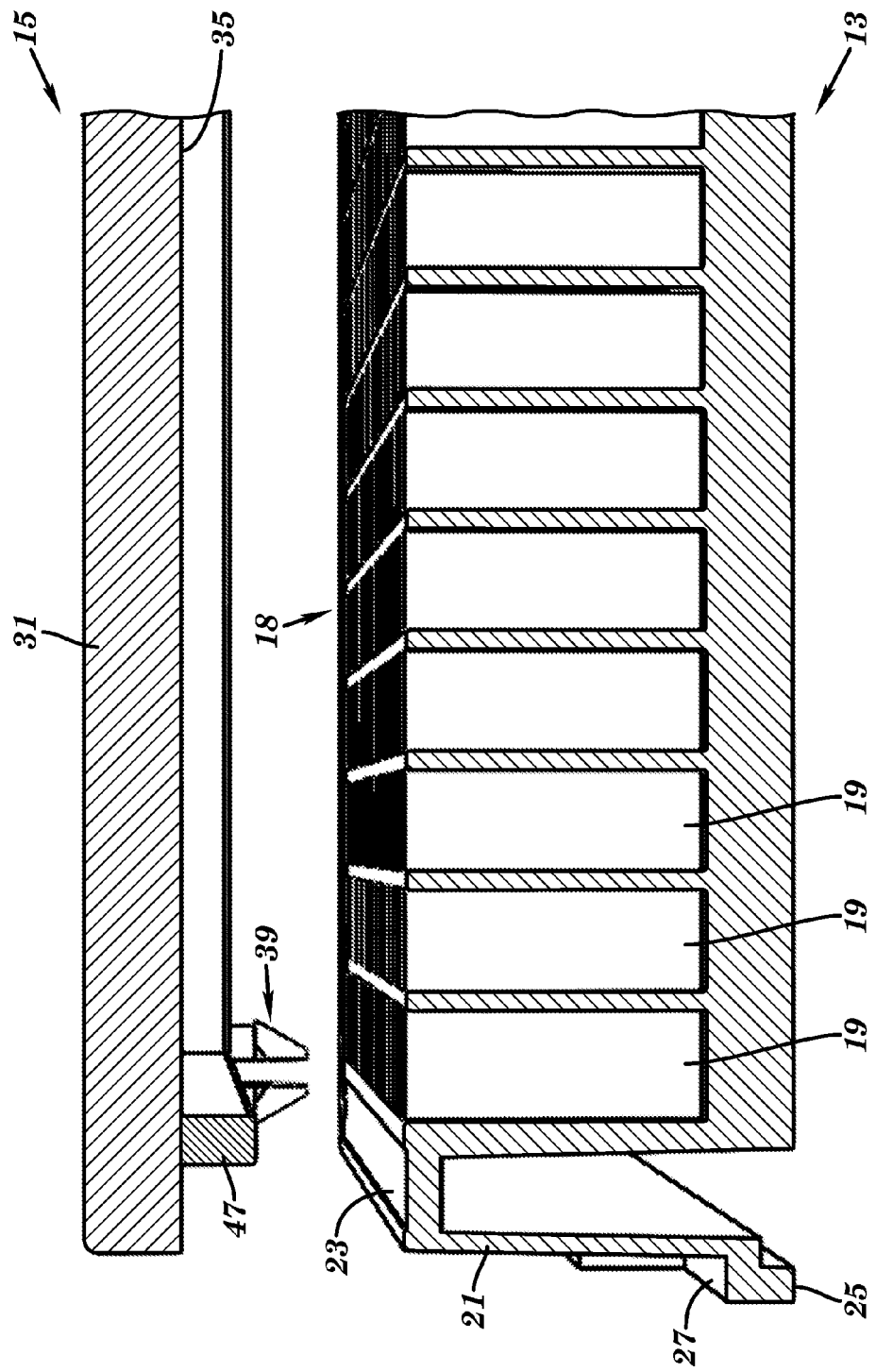
FIGS. 5(a) and 5(b) are fragmentary section views of the microplate and lid shown in FIG. 4(a), taken along lines 5-5, at various stages during the process of mounting the lid onto the microplate.

A hollow outer frame, or sidewall, 21 is formed directly around the periphery of sample area 18, sidewall 21 having an inverted U-shaped configuration in lateral cross-section (as seen most clearly in FIG. 5(a)). Sidewall 21 is shaped to define a thin, substantially flat top surface 23, a substantially open bottom surface 25 and an outwardly extending registration edge, or flange, 27 along bottom surface 25. As can be appreciated, registration edge 27 facilitates the accurate positioning of microplate 13 in an automated environment.

Sidewall 21 is additionally shaped to define a plurality of vertically disposed openings, or holes, 29 in top surface 23, with one hole 29 located in each corner of sidewall 21, as seen most clearly in FIG. 2. It should be noted that each hole 29 is generally circular in lateral cross-section, extends completely through top surface 23 and is accessible from the underside of microplate 13 (i.e., through substantially open bottom surface 25). As will be described further in detail below, lid 15 is releasably secured to microplate 13 through holes 29.

Figure 3:
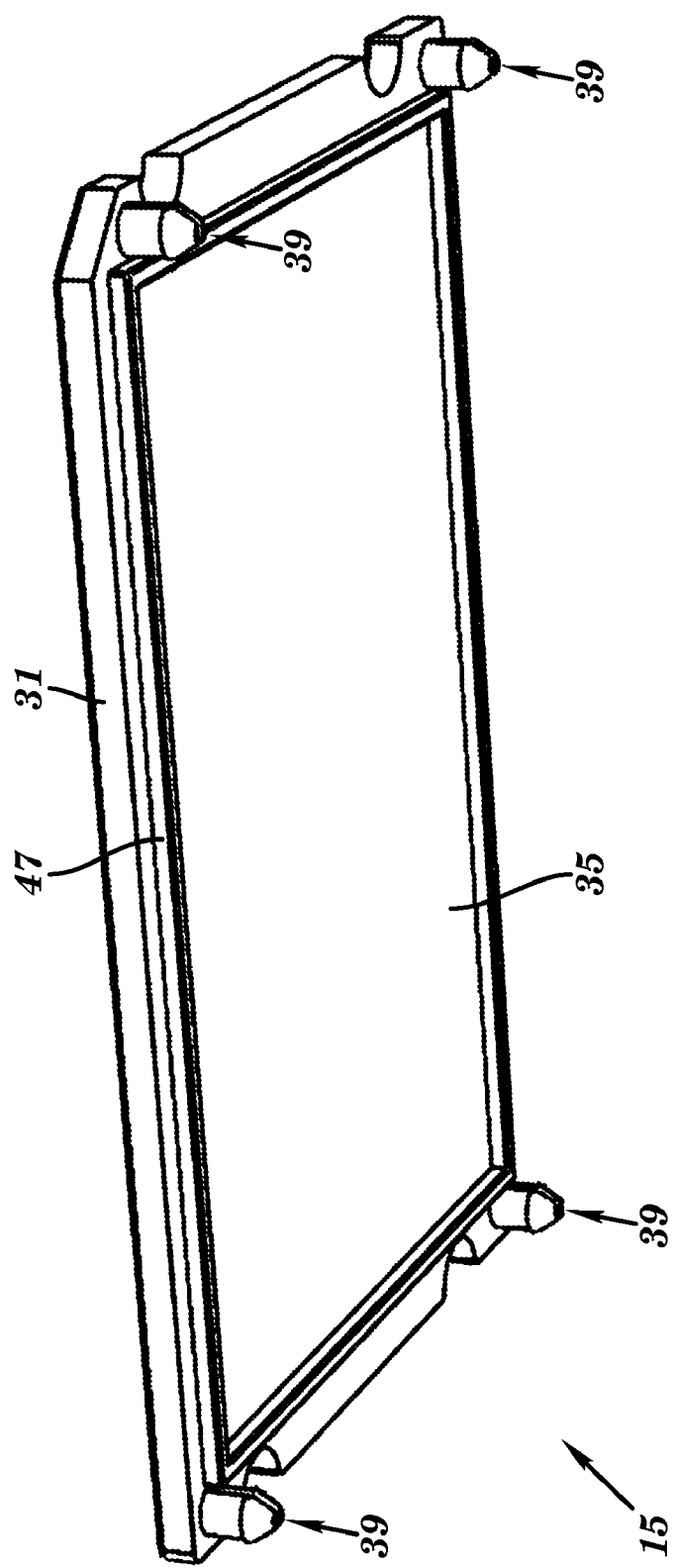
FIG. 3 is a bottom perspective view of the lid shown in FIG. 2.

As seen most clearly in FIGS. 2 and 3, lid 15 preferably comprises a thin, generally rectangular plate 31 which includes a substantially flat top surface 33 and a substantially flat bottom surface 35. Preferably, a plurality of arcuate notches 37 are formed along the outer edge of plate 31 to (i) facilitate handling of lid 15 and (ii) provide access to top surface 23 of sidewall 21 when lid 15 is mounted on microplate 13, as will described in further detail below.

Figure 4A:
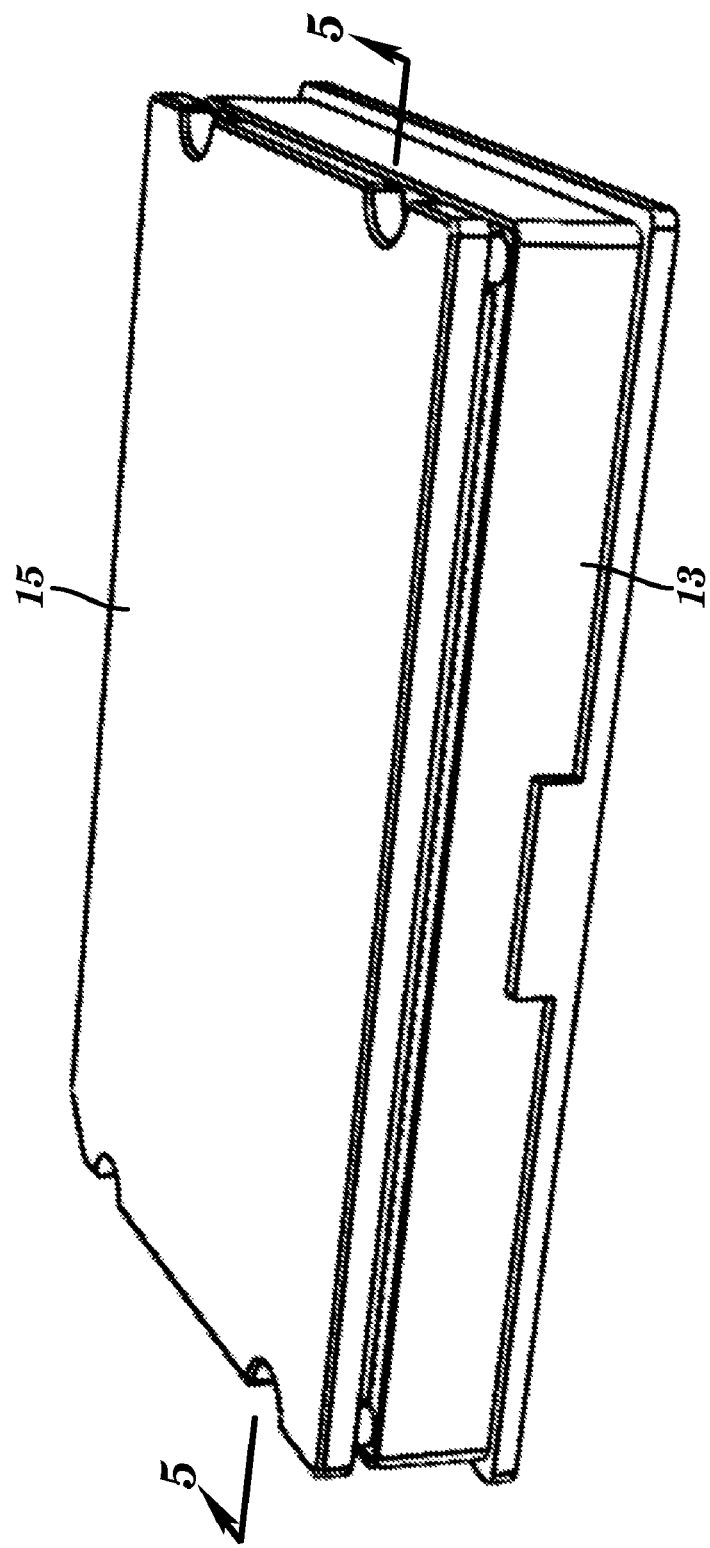
FIGS. 4(a) and 4(b) are front, top perspective and left end, top perspective views, respectively, of the microplate and lid shown in FIG. 2, the lid being shown mounted on the microplate.
Figure 4B:
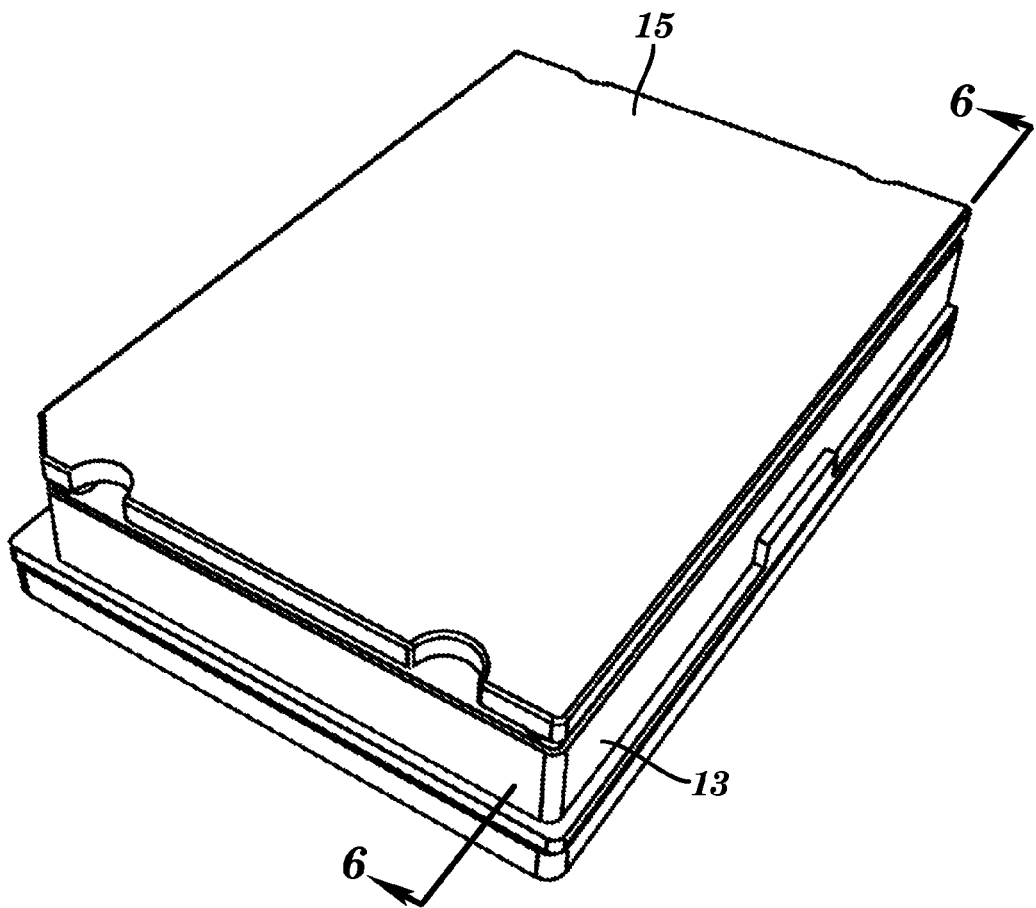

As seen most clearly in FIG. 3, a plurality of vertical projections, or latches, 39 extend orthogonally out from bottom surface 35 of plate 31, each latch 39 being represented herein as having a compressible, arrowhead-style design. Preferably, plate 31 and latches 39 are integrally formed together out of a plastic material through conventional molding techniques. As will be described further below, each latch 39 is dimensioned to snap-mount through a corresponding hole 29 in microplate 13. In this manner, lid 15 can be used to cover microplate 13, as seen most clearly in FIGS. 4(a) and 4(b).

Figure 6A:
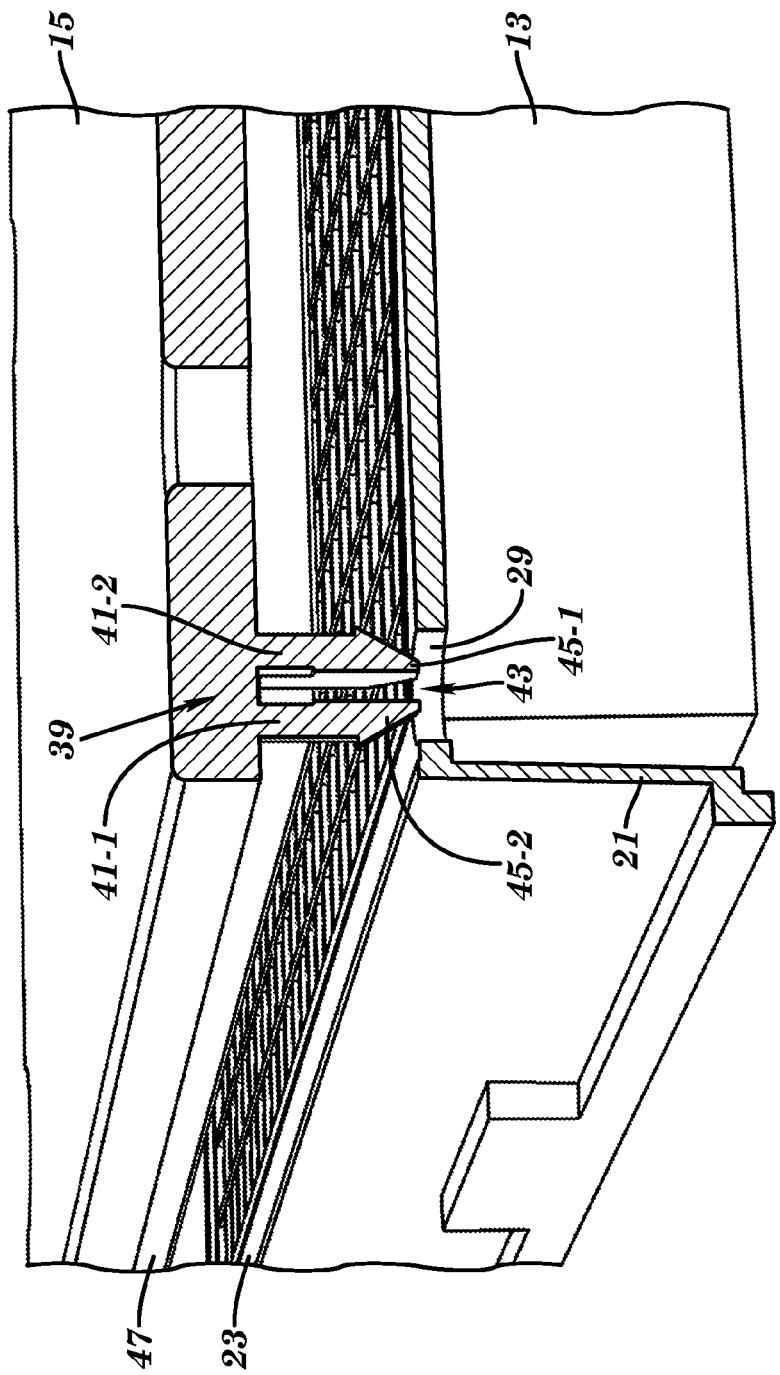
FIGS. 6(a)-(c) are fragmentary section views of the microplate and lid shown in FIG. 4(b), taken along lines 6-6, at various stages during the process of mounting the lid onto the microplate.

As seen most clearly in FIG. 6(a), each latch 39 is shaped to include a pair of semi-cylindrical legs 41-1 and 41-2 which are spaced slightly apart from one another so as to define a narrow slot 43 therebetween. A pair of outwardly extending barbs 45-1 and 45-2 are formed on the free ends of legs 41-1 and 41-2, respectively, the function of each barb 45 to become apparent below.

Figure 5B:
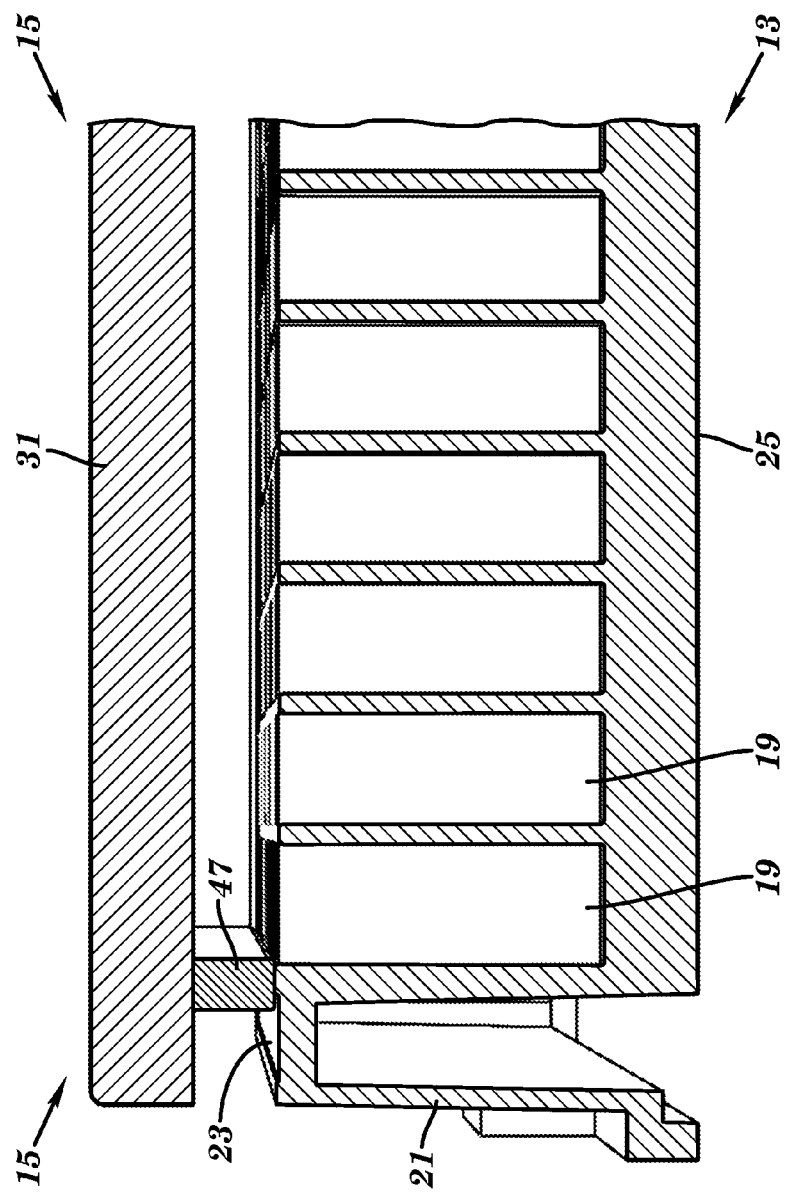

Referring back to FIG. 3, an open rectangular gasket 47 is affixed to bottom surface 35 in close proximity to the periphery of lid 15. Gasket 47 is preferably constructed out of a highly compliant, chemical resistant material. Accordingly, as lid 15 is mounted on microplate 13, gasket 47 is disposed firmly in contact against top surface 23, as seen most clearly in FIGS. 5(a) and 5(b). Preferably, lid 15 is mounted on microplate 13 with such force that gasket 47 compresses considerably, with latches 39 engaging microplate 13 to retain lid 15 firmly mounted on microplate 13. In this manner, it is to be understood that together gasket 47 and plate 31 effectively seal off wells 19 from the outside environment, which is highly desirable.

Gasket 47 is represented herein as having an O-ring style (i.e., an open rectangular configuration that extends along the periphery of plate 31). In this manner, each well 19 is sealed off from the outside environment but is remains in fluid communication with the remaining wells 19 in microplate 13, as seen most clearly in FIG. 5(b). Accordingly, it is to be understood that alternative styles of gaskets could be used in place thereof without departing from the spirit of the present invention. For example, gasket 47 could be replaced by a single sheet gasket (i.e., a solid, or closed, rectangular gasket) that would serve to seal off each individual well 19 in microplate 13, which may be desirable in certain applications.

Figure 6B:
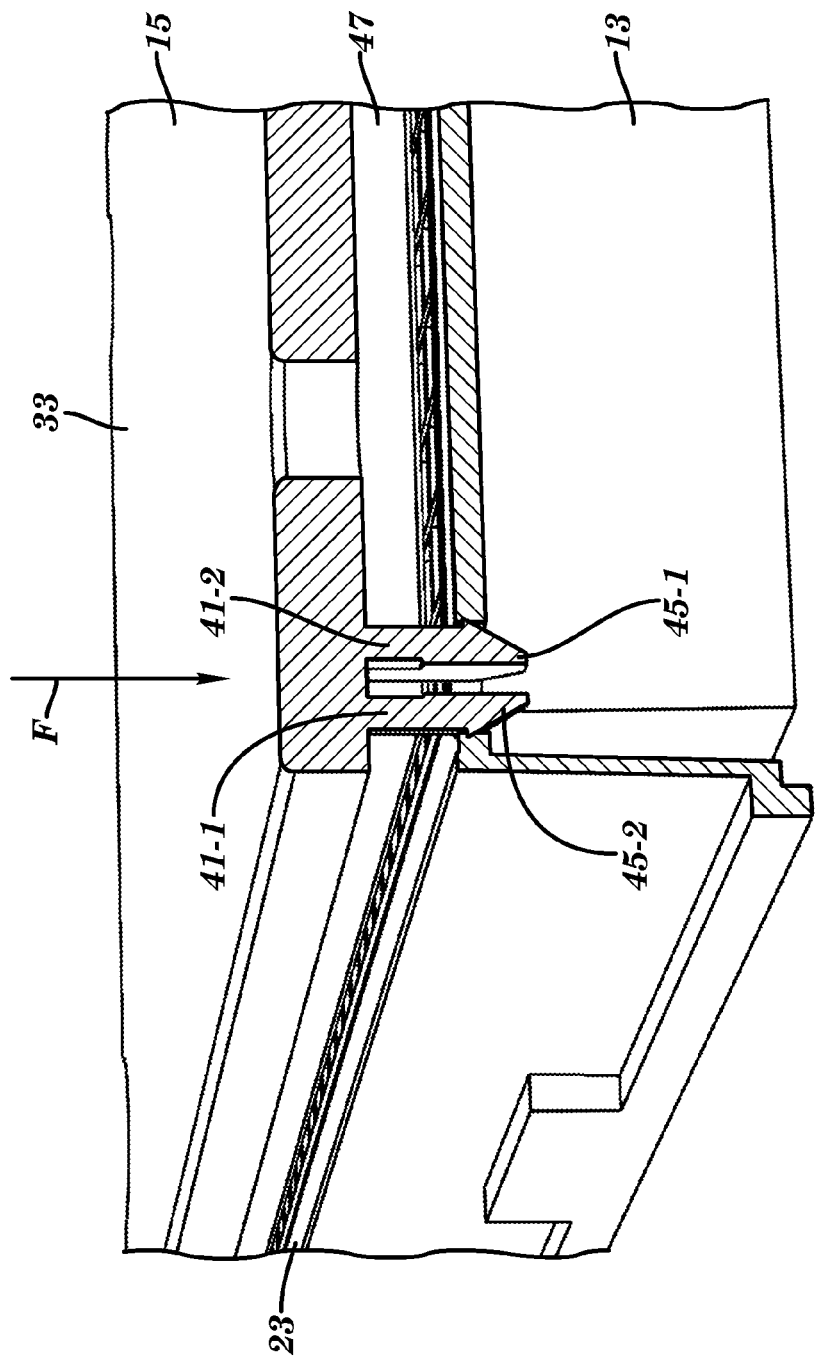
Figure 6C:
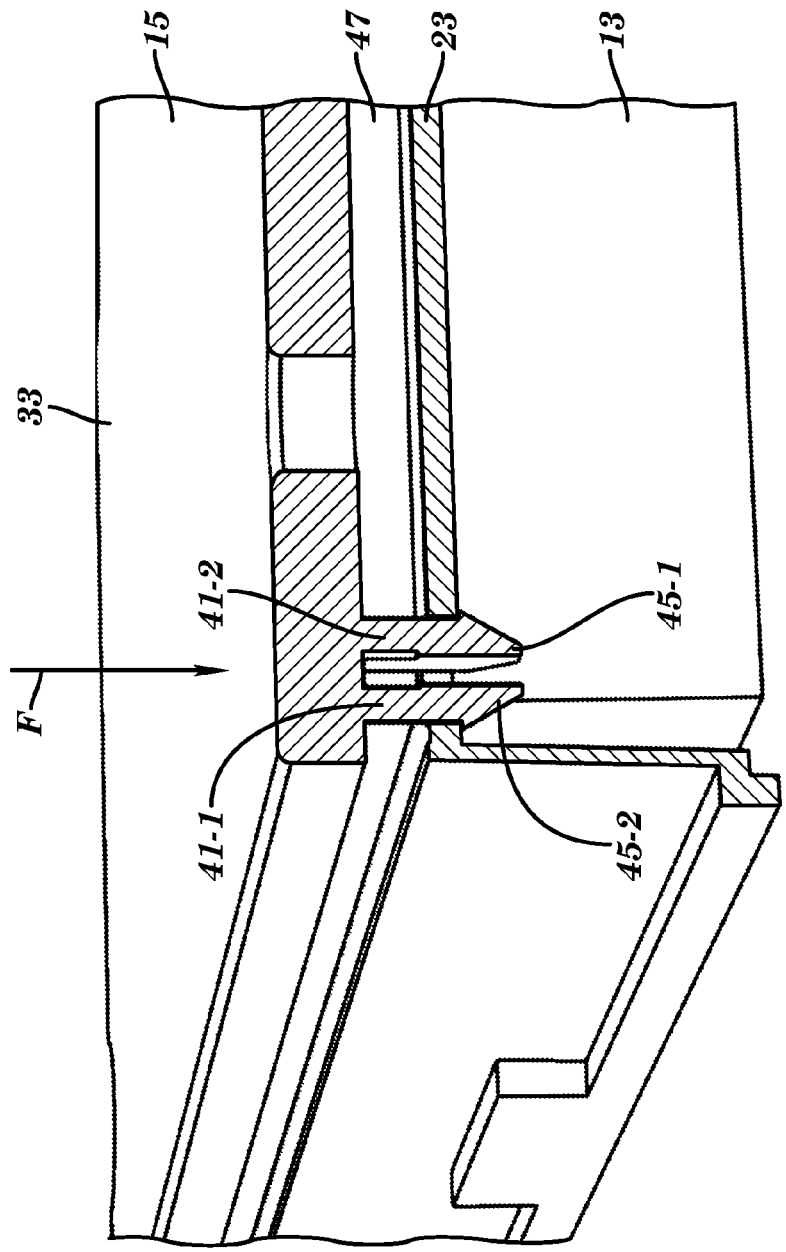

Referring now to FIGS. 6(a)-(c), there is shown a section view of microplate 13 at various stages during the process of mounting lid 15 thereon. In the first step of the lidding process, lid 15 is positioned above microplate 13 with each latch 39 disposed in coaxial alignment with a corresponding hole 29 in top surface 23 of microplate 13, as shown in FIG. 6(a).

Aligned as such, a downward force F is applied onto top surface 33 of lid 15 using manual or automated means, as shown in FIG. 6(b). The downward force applied to lid 15 urges barbs 45-1 and 45-2 of each latch 39 into direct contact against the portion of top surface 23 that immediately surrounds each hole 29. Due to the inclusion of slot 43, the downward force causes each latch 39 to compress to the extent necessary so that barbs 45-1 and 45-2 can pass through each hole 29.

As seen most clearly in FIG. 6(c), the continued application of force F onto top surface 33 of lid 15 ultimately causes barbs 45-1 and 45-2 to penetrate entirely through hole 29. At this point, legs 41-1 and 41-2 of each latch 39 snap resiliently back into their original configuration, with barbs 45-1 and 45-2 of each latch 39 firmly engaged against the underside of top surface 23. In this manner, it is to be understood that latches 39 serve to lockably retain lid 15 tightly in place on microplate 13, which is highly desirable.

As can be appreciated, the particular design of lid 15 introduces a number of notable advantages over prior art methods of sealing microplates.

As a first benefit, microplate lid 15 is relatively inexpensive to manufacture. To the contrary, many well-known microplate lids and sealing methods use either expensive materials (e.g., metals) or have complex designs.

As a second benefit, the snap-fastening engagement means between microplate 13 and lid 15 renders the above-described lidding process easy to accomplish. Furthermore, because the above-described lidding process requires only (i) the proper orientation of lid 15 relative to microplate 13 and (ii) the application of a suitable force F onto lid 15, microplate 13 and lid 15 can be easily integrated into existing automated systems.

As a third benefit, the above-described design of lid 15 can be used in conjunction with a wide range of different microtitre plate sizes and densities, thereby increasing its range of potential applications.

As a fourth benefit, the particular design of lid 15 does not serve to increase the overall footprint (i.e., length and width) of the microplate 13, thereby rendering said components usable in most, if not all, preexisting automated systems.

As noted briefly above, tool 17 is designed to assist in the removal (i.e., or delidding) of lid 15 from microplate 13. Referring back to FIG. 1, tool 17 comprises a rigid, rectangular base 51 with the same approximate footprint as microplate 13, base 51 comprising a substantially flat top surface 53 and a substantially flat bottom surface 55.

Tool 17 additionally includes a plurality of support members, or posts, 57 which extend orthogonally away from top surface 53, posts 57 being located on base 51 in such a manner so that each post 57 coaxially aligns with a corresponding hole 29 in microplate 13, as will be described further below. It is to be understood that the free end of each post 57 is provided with an inwardly sloped, or concave, surface 59 which appears conical in lateral cross-section, as seen most clearly in FIG. 7(a), the function of concave surface 59 to become apparent below.

Figure 7A:
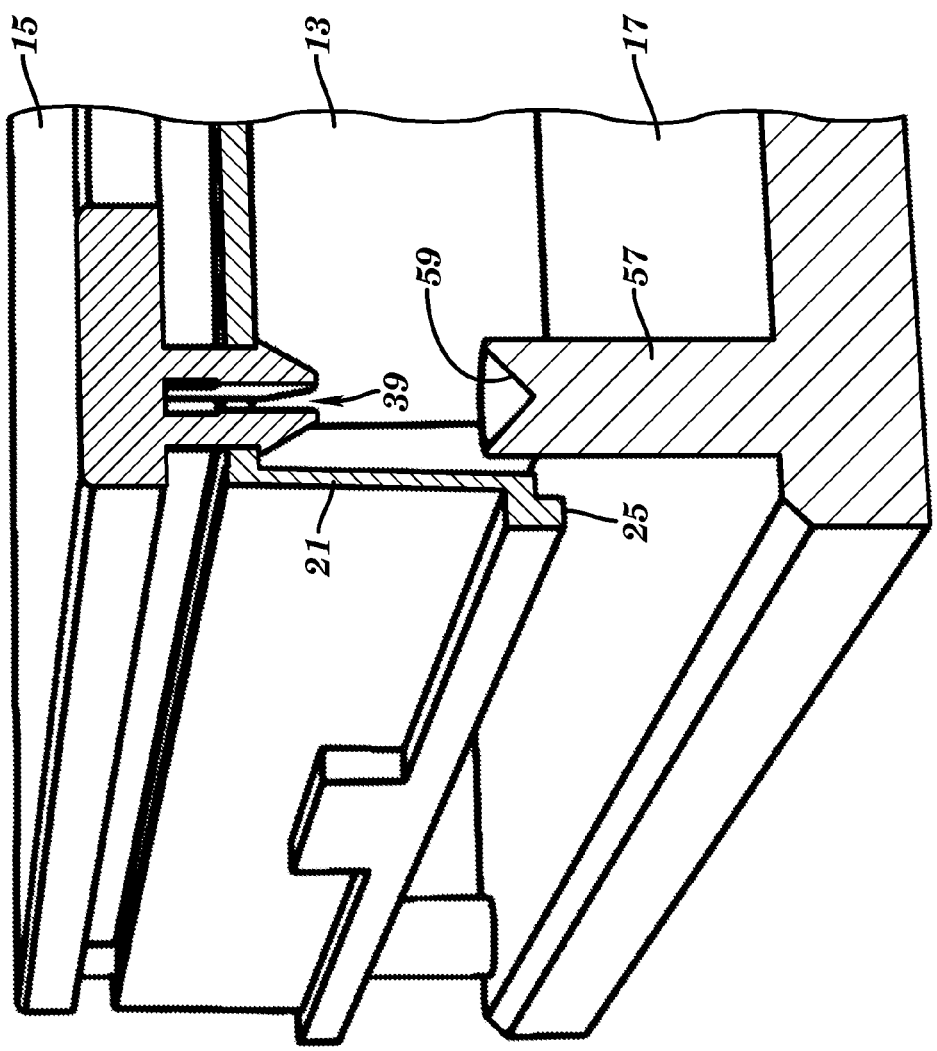
FIGS. 7(a)-(d) are fragmentary section views of the microplate kit shown in FIG. 1, taken along lines 7-7, at various stages during the process of removing the lid from the microplate using the lid removal tool.

Referring now to FIGS. 7(a)-(d), there is shown a section view of kit 11 at various stages during the process of removing lid 15 from microplate 13 using lid removal tool 17. With lid 15 firmly mounted on microplate 13 as described in detail above, tool 17 is positioned beneath microplate 13 in such a manner so that each post 57 projects up through substantially open bottom surface 25 in sidewall 21 and into direct coaxial alignment with a corresponding latch 39 on lid 15, as shown in FIG. 7(a).

Figure 7B:
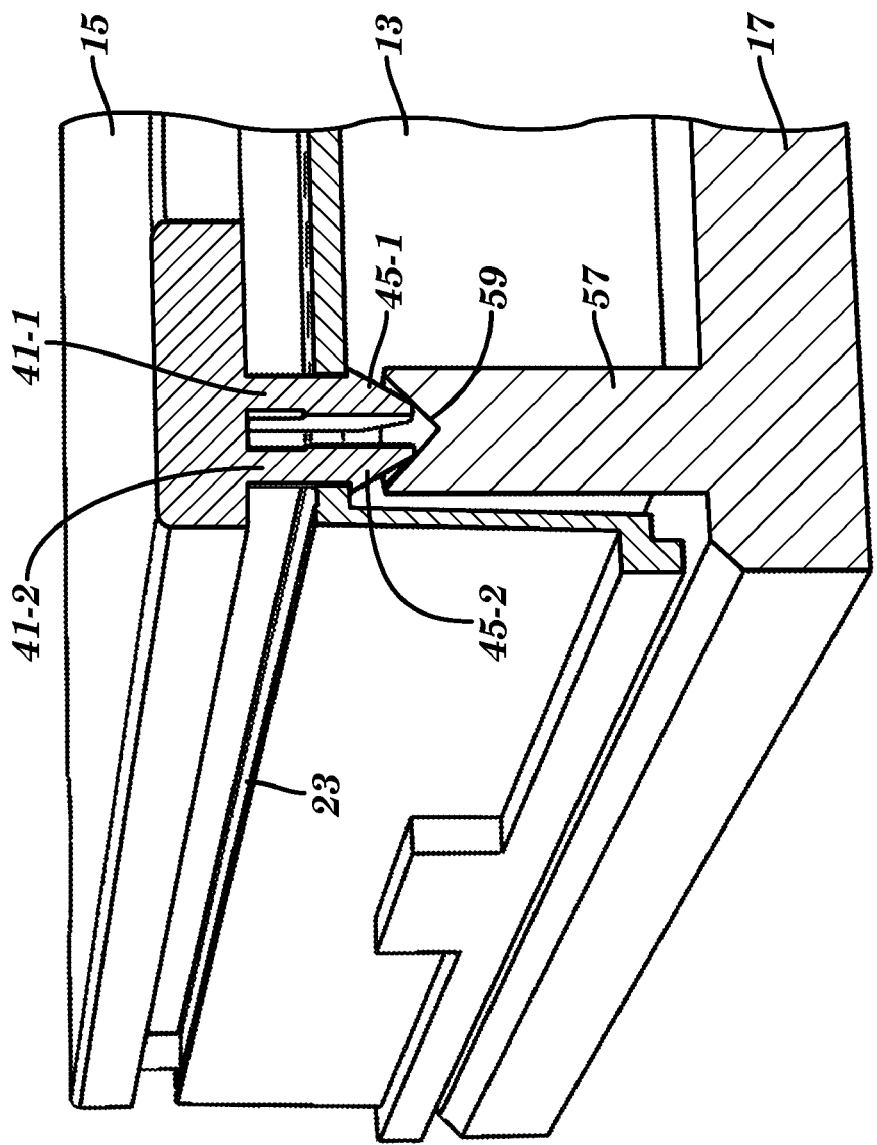
Figure 7C:
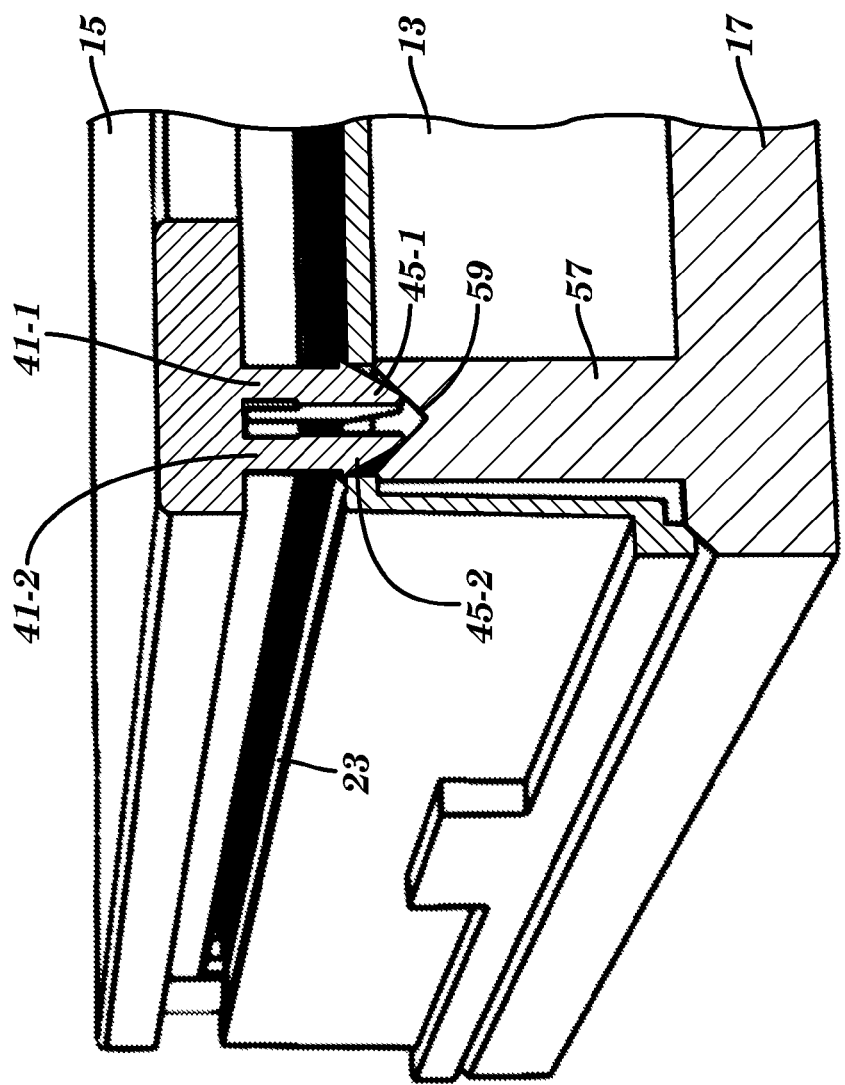
Figure 7D:
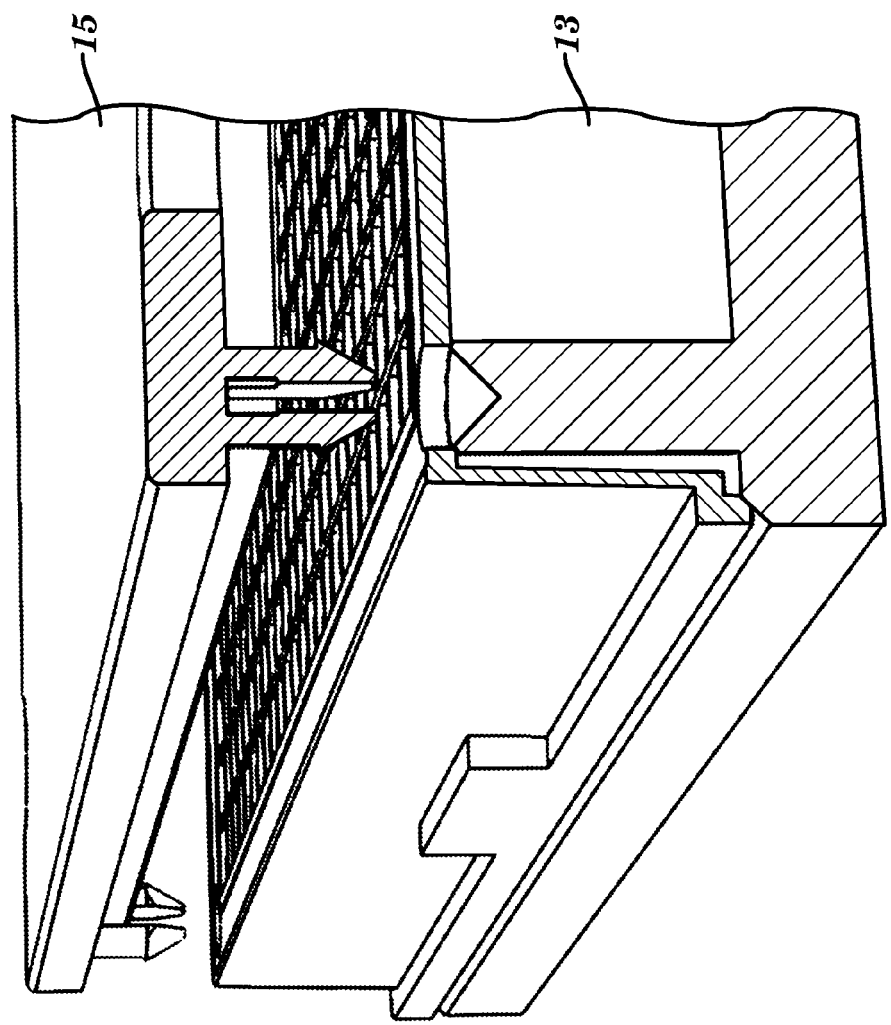

Aligned as such, microplate 13 is drawn down onto tool 17 until barbs 45-1 and 45-2 of each latch 39 directly contact concave surface 59 of a corresponding post 57 on tool 17, as shown in FIG. 7(b). At this time, a suitable downward force is applied to top surface 23 of microplate 13 (e.g., through notches 37) using manual or automated means. This downward force causes barbs 45-1 and 45-2 of each latch 39 to slide inward along concave surface 59 which in turn causes legs 41-1 and 41-2 to flex slightly inward (i.e., compressing latch 39).

As seen most clearly in FIG. 7 (c), the continued application of a downward force on top surface 23 of microplate 13 ultimately causes legs 41 of each latch 39 to flex inward to the extent necessary so that their corresponding barbs 45 disengage from the underside of top surface 23. This disengagement causes the barbs 45 for each latch 39 to withdraw from its associated hole 29 in microplate 13 and thereby release lid 15 from microplate 13. Disengaged lid 15 can then be fully separated from microplate 13 using either manual or automated means, as shown in FIG. 7(d). In this manner, it is to be understood that lid 15 can be repeatedly mounted/released from microplate 13 as deemed necessary, which is a principal object of the present invention.

Figure 8:
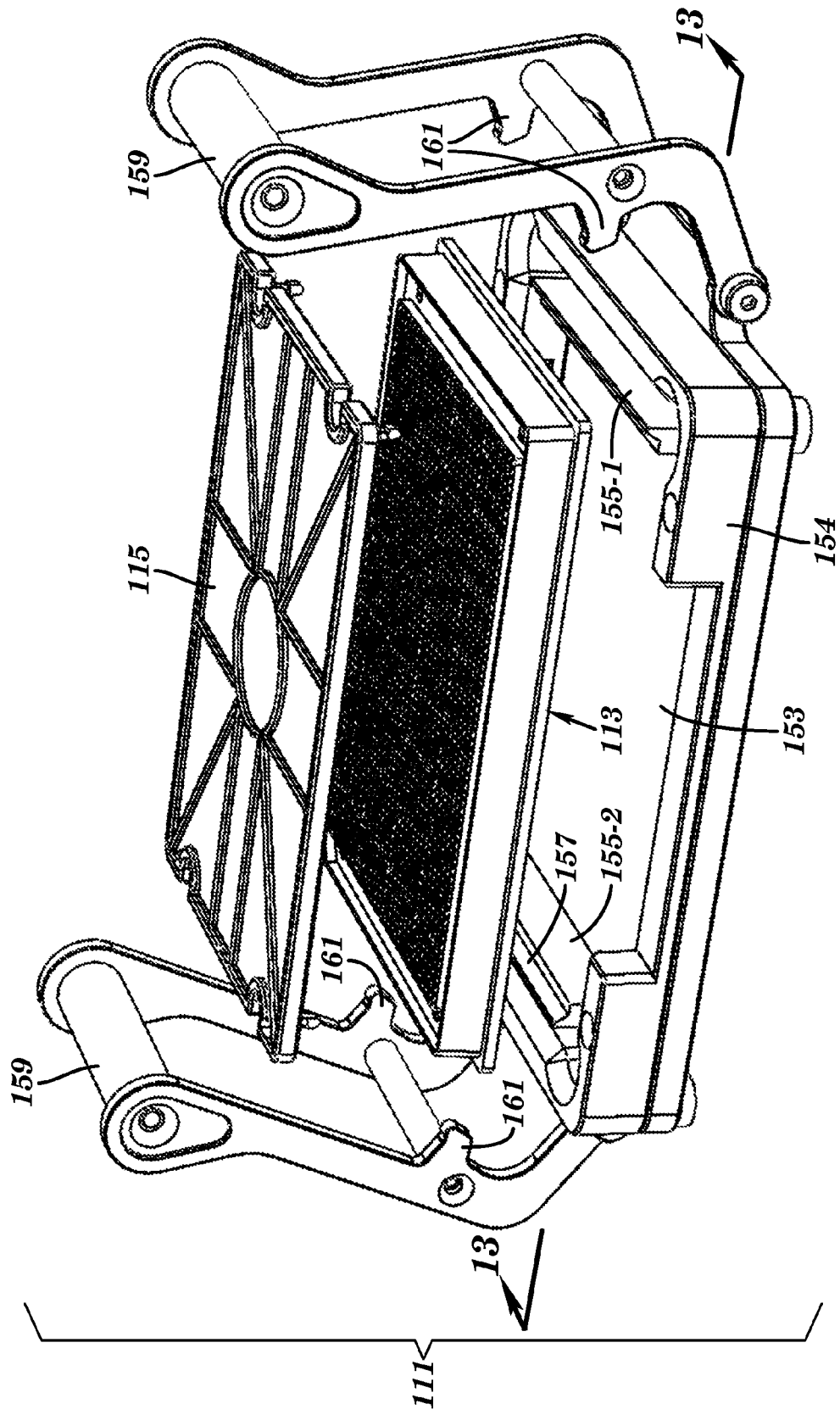
FIG. 8 is an exploded, top perspective view of a second embodiment of a microplate kit constructed according to the teachings of the present invention.

Referring now to FIG. 8, there is shown an exploded, top perspective view of a second embodiment of a microplate kit that is constructed according to the teachings of the present invention and identified generally by reference numeral 111.

Microplate kit 111 is similar to microplate kit 11 in that microplate kit 111 comprises a microplate 113, a lid 115 designed to be removably mounted onto microplate 113 and a tool 117 designed to assist in the removal of lid 115 when mounted on microplate 113.

Figure 9:
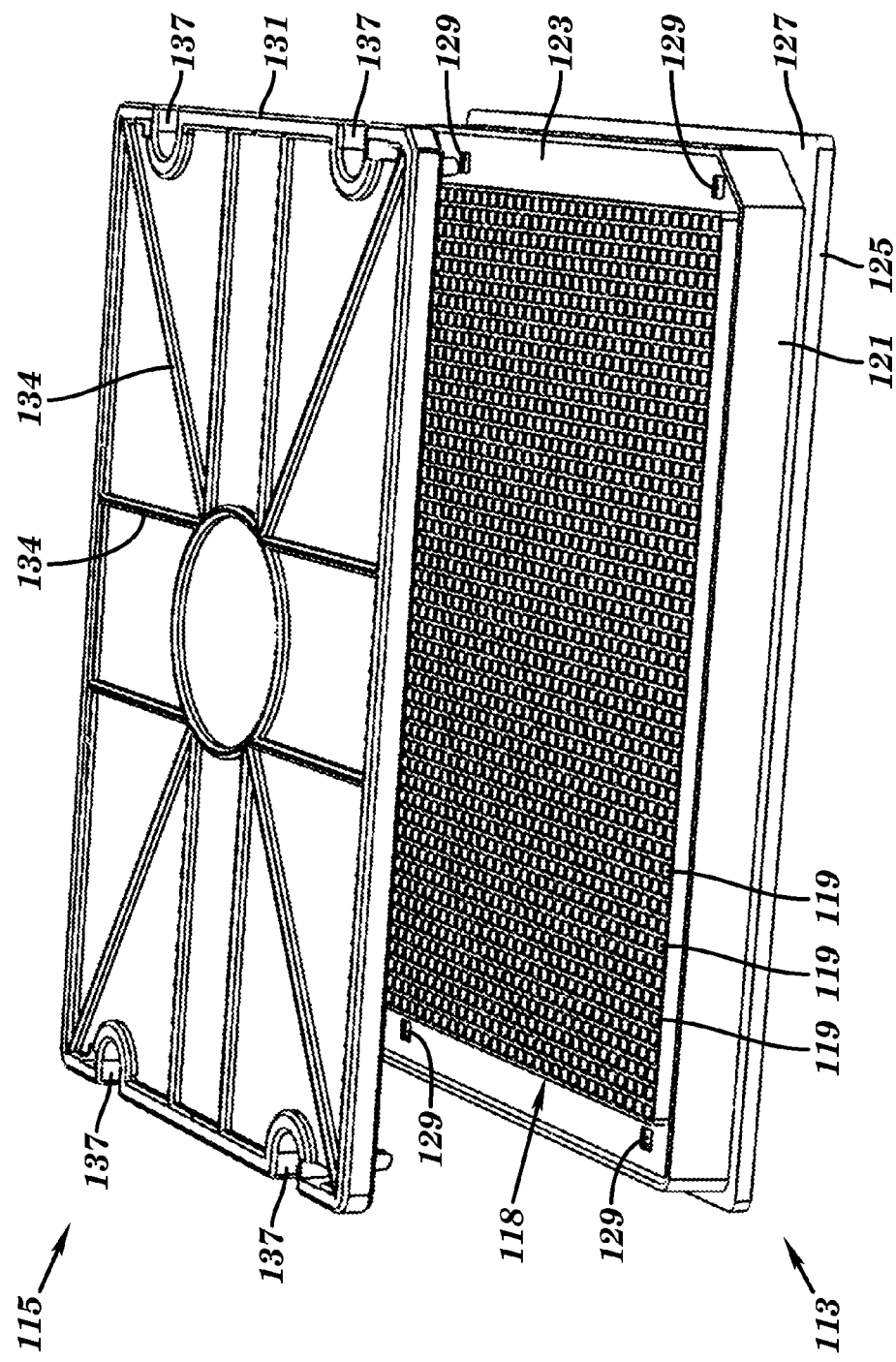
FIG. 9 is an exploded, top perspective view of the microplate and lid shown in FIG. 8.

Referring now to FIG. 9, microplate 113 is similar to microplate 13 in that microplate 113 is generally block-shaped in its design and includes an enlarged sample area 118 that is provided with a plurality of individual, vertically-disposed wells 119. Microplate 113 similarly includes a hollow outer frame, or sidewall, 121 that is formed directly around the periphery of sample area 118, sidewall 121 having an inverted U-shaped configuration in lateral cross-section (as seen most clearly in FIG. 12(a)). Specifically, sidewall 121 is shaped to define a thin, substantially flat top surface 123, a substantially open bottom surface 125 and an outwardly extending registration edge, or flange, 127 along bottom surface 125. Furthermore, sidewall 121 is additionally shaped to define a plurality of vertical holes 129 in top surface 123, with one hole 129 located in each corner of sidewall 121, as seen most clearly in FIG. 9.

It should be noted that microplate 113 differs from microplate 13 principally in that (i) microplate 113 includes a higher density of wells 119 (notably, 1536 wells as opposed to 384 wells in microplate 13) and (ii) microplate 113 includes holes 129 which are generally rectangular in lateral cross-section (as opposed to the circular holes 29 in microplate 13).

Figure 10:
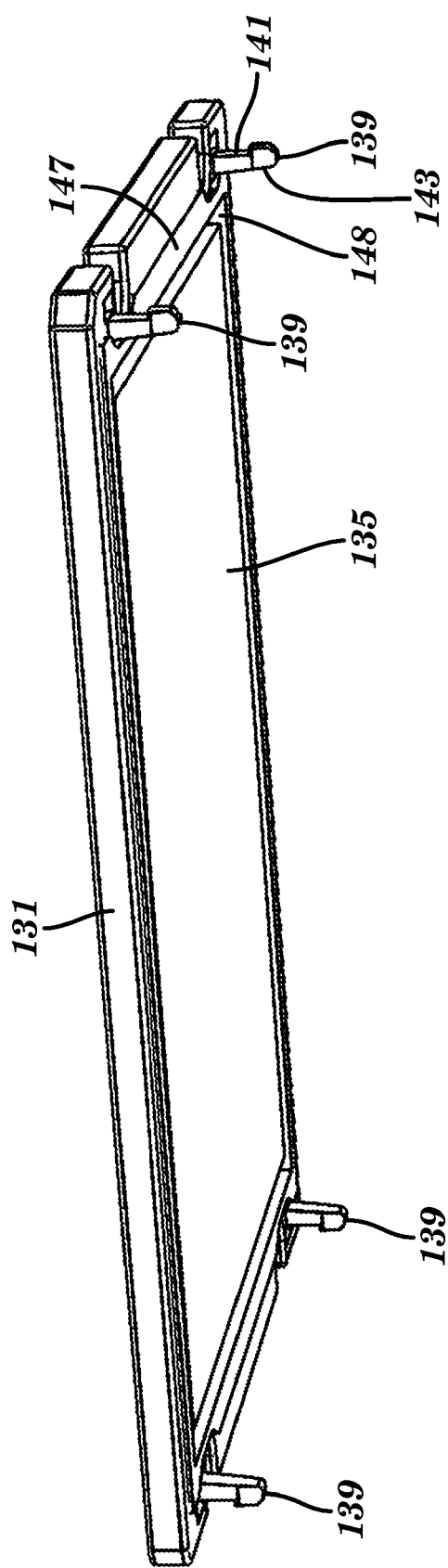
FIG. 10 is a bottom perspective view of the lid shown in FIG. 9.
Figure 12A:
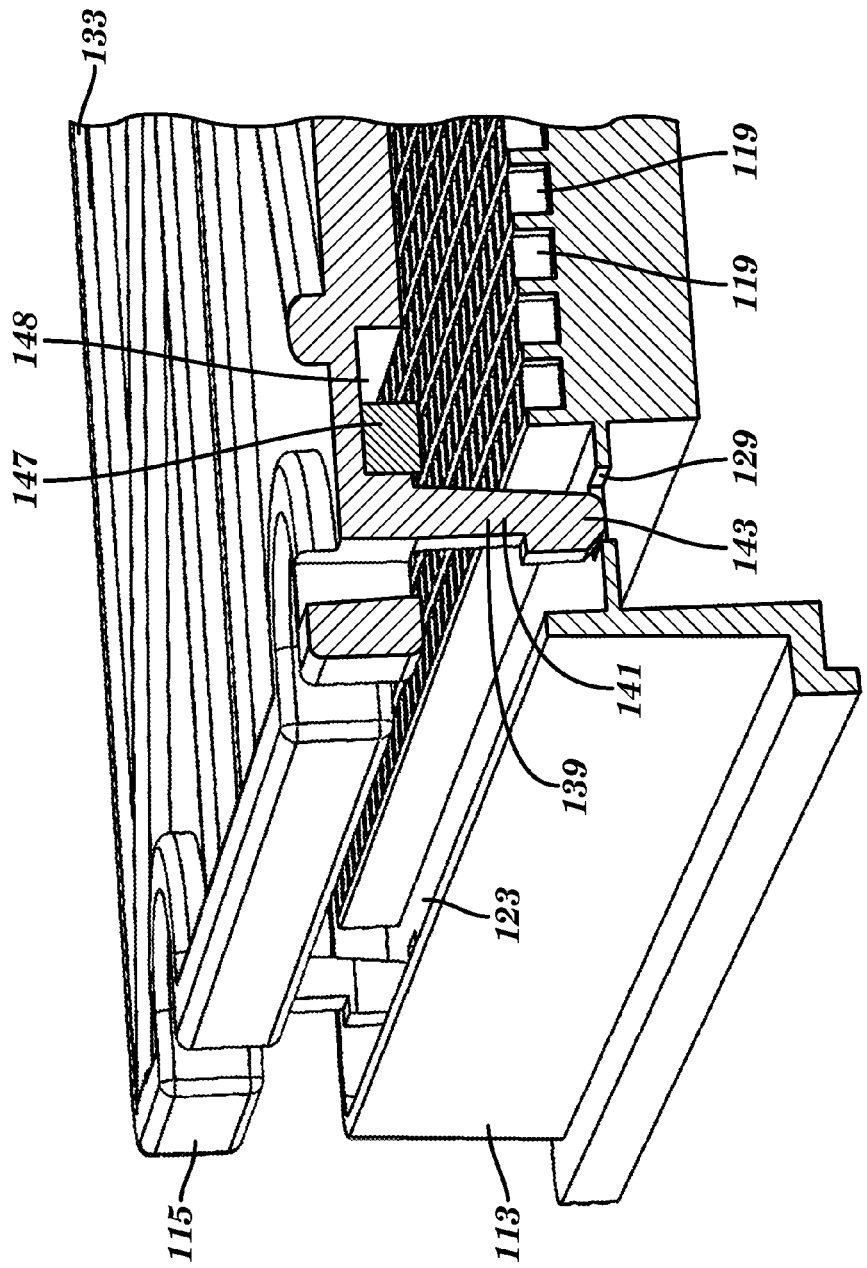
FIGS. 12(a)-(c) are fragmentary section views of the microplate and lid shown in FIG. 11, taken along lines 12-12, at various stages during the process of mounting the lid onto the microplate.

As seen most clearly in FIGS. 9, 10 and 12(a), lid 115 is similar to lid 15 in that lid 115 comprises a thin, generally rectangular plate 131 which includes a top surface 133, a bottom surface 135 and a plurality of arcuate notches 137 formed along its outer edge. It should be noted that the majority of top surface 133 is preferably recessed to reduce the amount of plastic required for its construction. A plurality of strengthening ribs 134 is preferably formed into top surface 133 to provide lid 115 with the necessary structural rigidity.

Lid 115 differs from lid 15 principally in that lid 115 comprises a plurality of vertical projections, or latches, 139 which are different in construction than latches 39. Specifically, each latch 139 is represented herein as being in the form of a single, deflectable arm 141 which extends orthogonally out from bottom surface 135 of plate 31, the free end of each arm 141 being shaped to include an enlarged engagement barb 143. In use, latches 139 operate in a similar manner as latches 39 in that latches are dimensioned to snap-mount through corresponding openings 129 in microplate 113, as will be described further in detail below.

Figure 11:
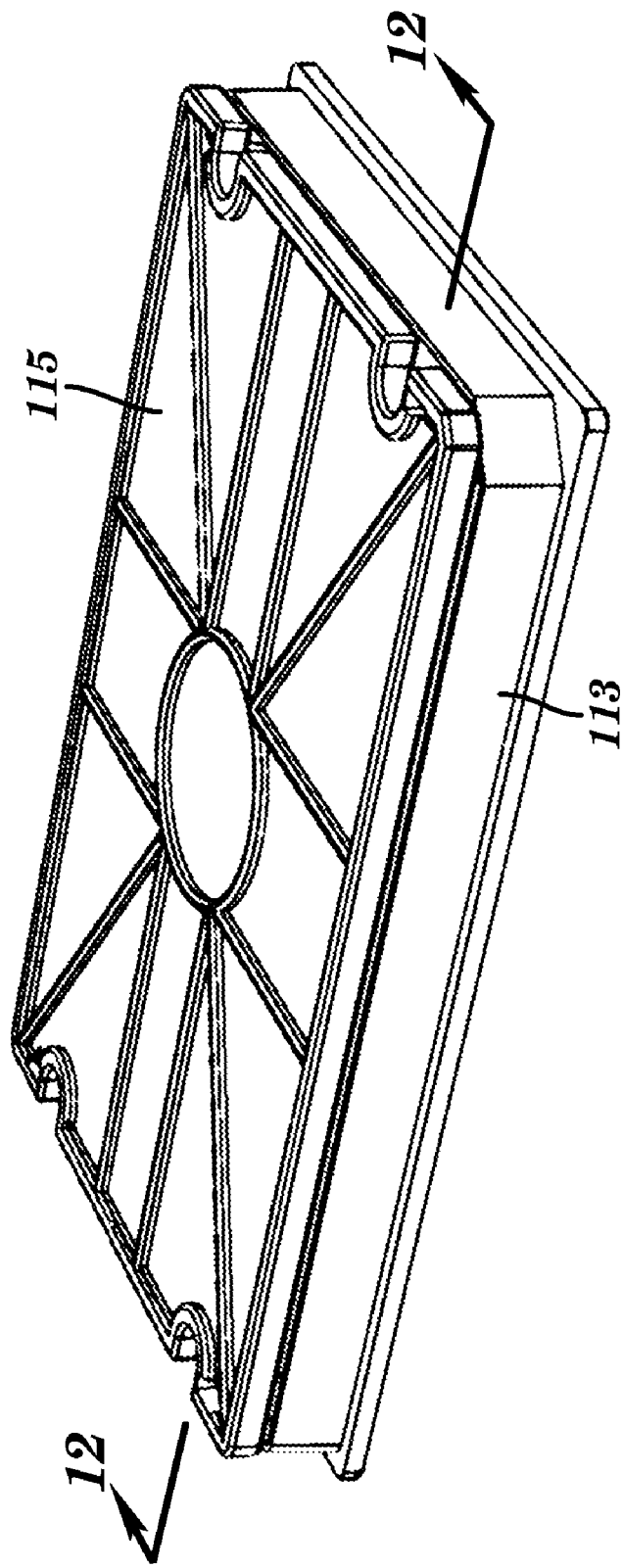
FIG. 11 is a top perspective view of the microplate and lid shown in FIG. 9, the lid being shown mounted on the microplate.

As seen most clearly in FIGS. 10 and 12(a), an open rectangular gasket 147 is secured within a corresponding rectangular groove 148 formed in bottom surface 135. Gasket 147 is similar to gasket 47 in that, with lid 115 is mounted on microplate 113 (as represented in FIG. 11), gasket 147 compresses to the extent necessary to adequately seal wells 119 from the outside environment.

Figure 12B:
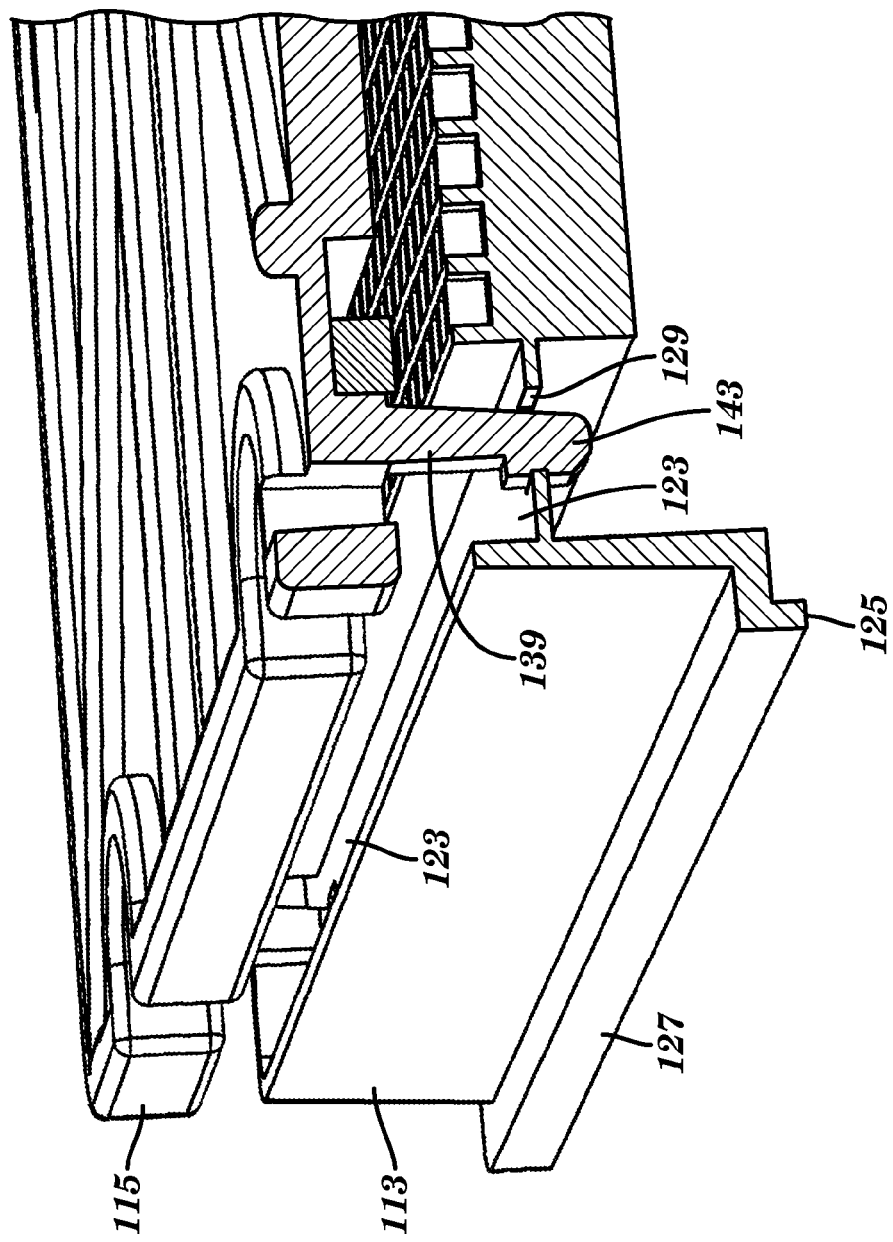
Figure 12C:
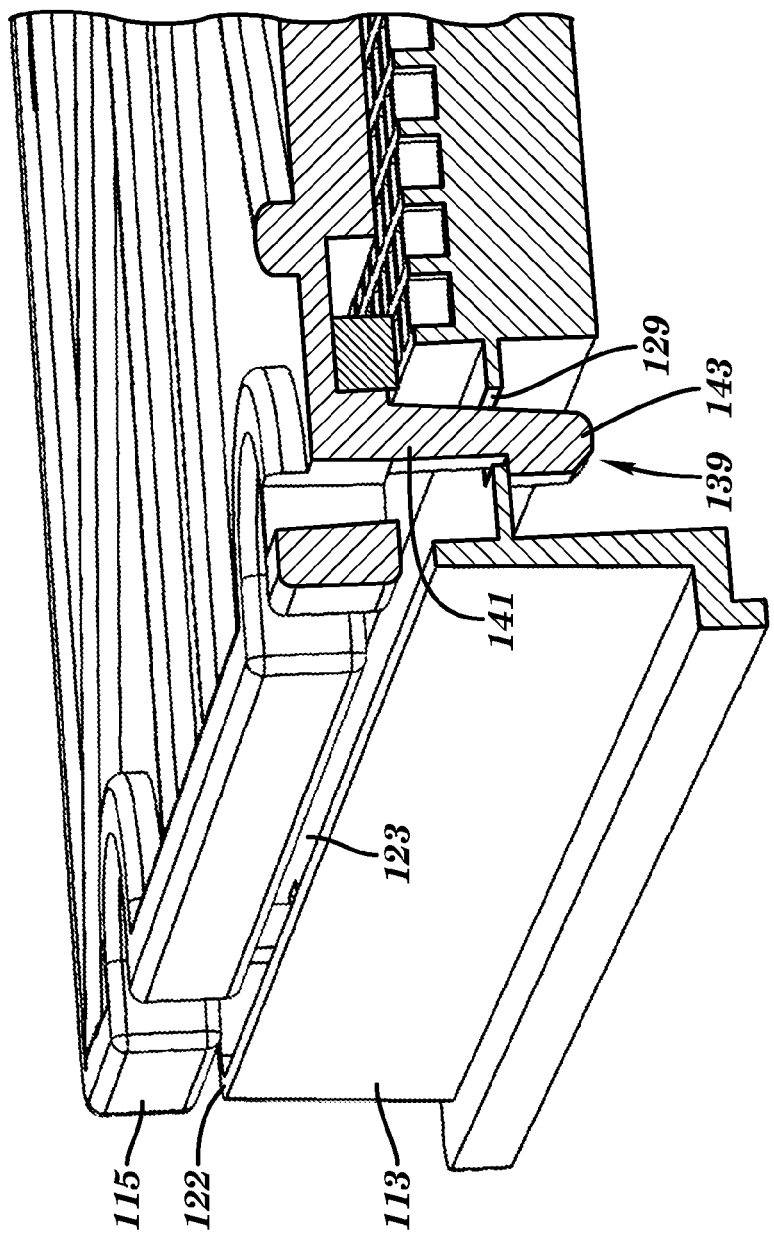

Referring now to FIGS. 12(a)-(c), there is shown a section view of microplate 113 at various stages during the process of mounting lid 115 thereon. In the first step of the lidding process, lid 115 is positioned above microplate 113 with each latch 139 disposed in coaxial alignment with a corresponding hole 129 in top surface 123 of microplate 113, as shown in FIG. 12(a).

Aligned as such, a downward force is applied onto top surface 133 of lid 115. The downward force applied to lid 115 deflects each latch 139 inward to the extent necessary for its enlarged barb 143 to insert into its corresponding hole 129 in microplate 113, as seen in FIG. 12(b). The continued application of downward force onto top surface 133 of lid 115 ultimately causes barb 143 of each latch 139 to penetrate entirely through its corresponding hole 129. Once barb 143 of each latch 139 passes through its corresponding hole 129, latch 139 resiliently snaps back into its original configuration, with barb 143 firmly engaged against the underside of top surface 123, as shown in FIG. 12(c). In this manner, it is to be understood that latches 139 are similar in function with latches 39 in that latches 139 serve to lockably retain lid 115 tightly in place on microplate 113, which is highly desirable.

Tool 117 functions in a similar manner as tool 17 in that tool 117 can be used to deflect latches 139 inward to the extent necessary so that lid 115 can be disengaged and subsequently removed from microplate 113. Referring back to FIG. 8, tool 117 comprises a flat, rectangular base 153 and an upstanding sidewall 154 formed along the periphery of base 153. A pair of elongated support members 155-1 and 155-2 project orthogonally upward from opposite ends of the top surface of base 153, each support member 155 being shaped to include an angled, or tapered, top surface 157. In addition, a pair of opposing handles 159 are pivotally connected to base 153, each handle 159 being shaped to include a pair of inwardly protruding fingers 161, the function of fingers 161 to become apparent below.

Figure 13A:
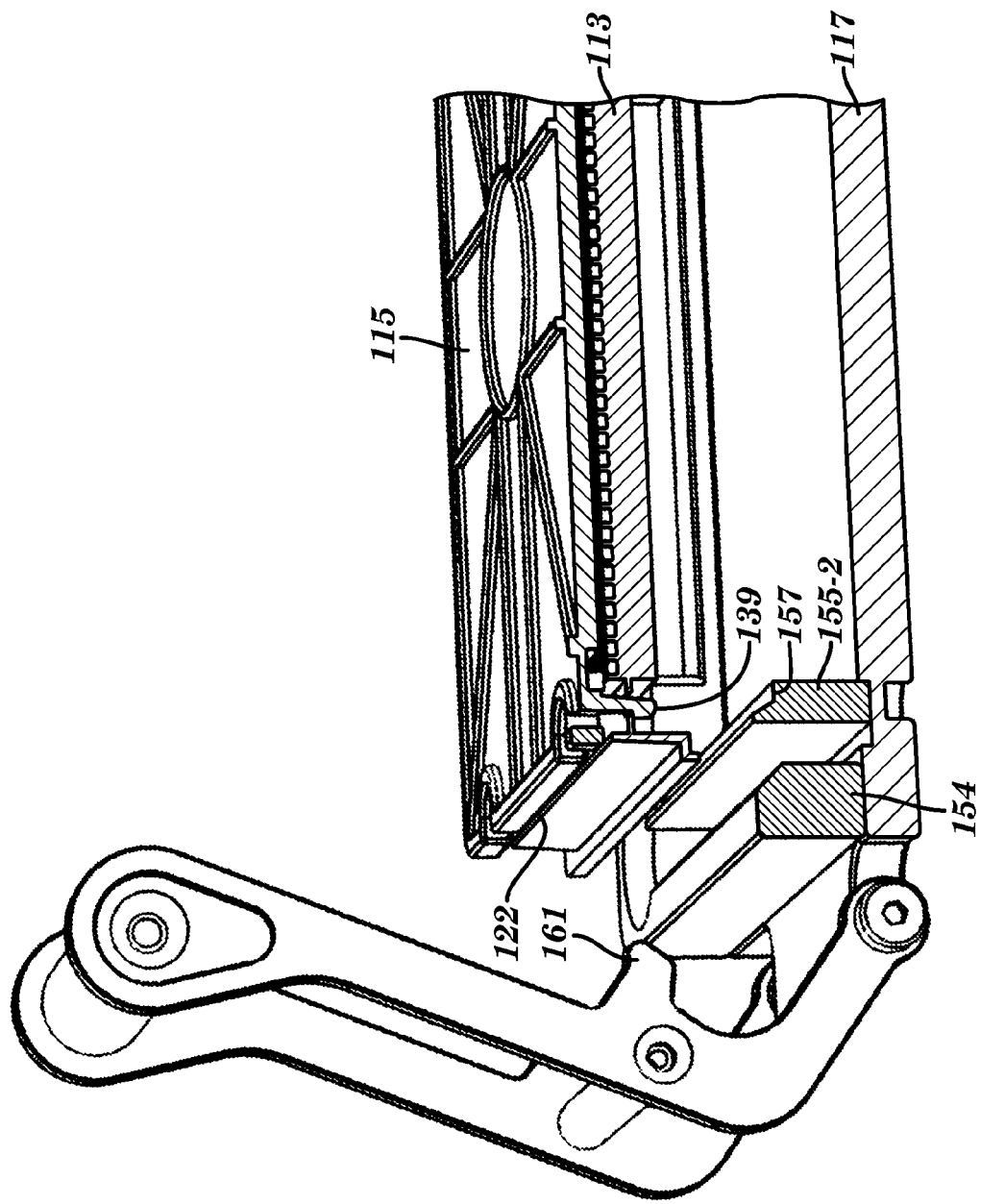
FIGS. 13(a)-(d) are fragmentary section views of the microplate kit shown in FIG. 8, taken along lines 13-13, at various stages during the process of removing the lid from the microplate using the lid removal tool.

Referring now to FIGS. 13(a)-(d), there is shown a section view of kit 111 at various stages during the process of removing lid 115 from microplate 113 using lid removal tool 117. With lid 115 firmly mounted on microplate 113 as described in detail above, tool 117 is positioned beneath microplate 113 in such a manner so that top surface 157 of each support member 155 is disposed in direct alignment beneath a corresponding pair of latches 139 on lid 115, as shown in FIG. 13(a).

Figure 13B:
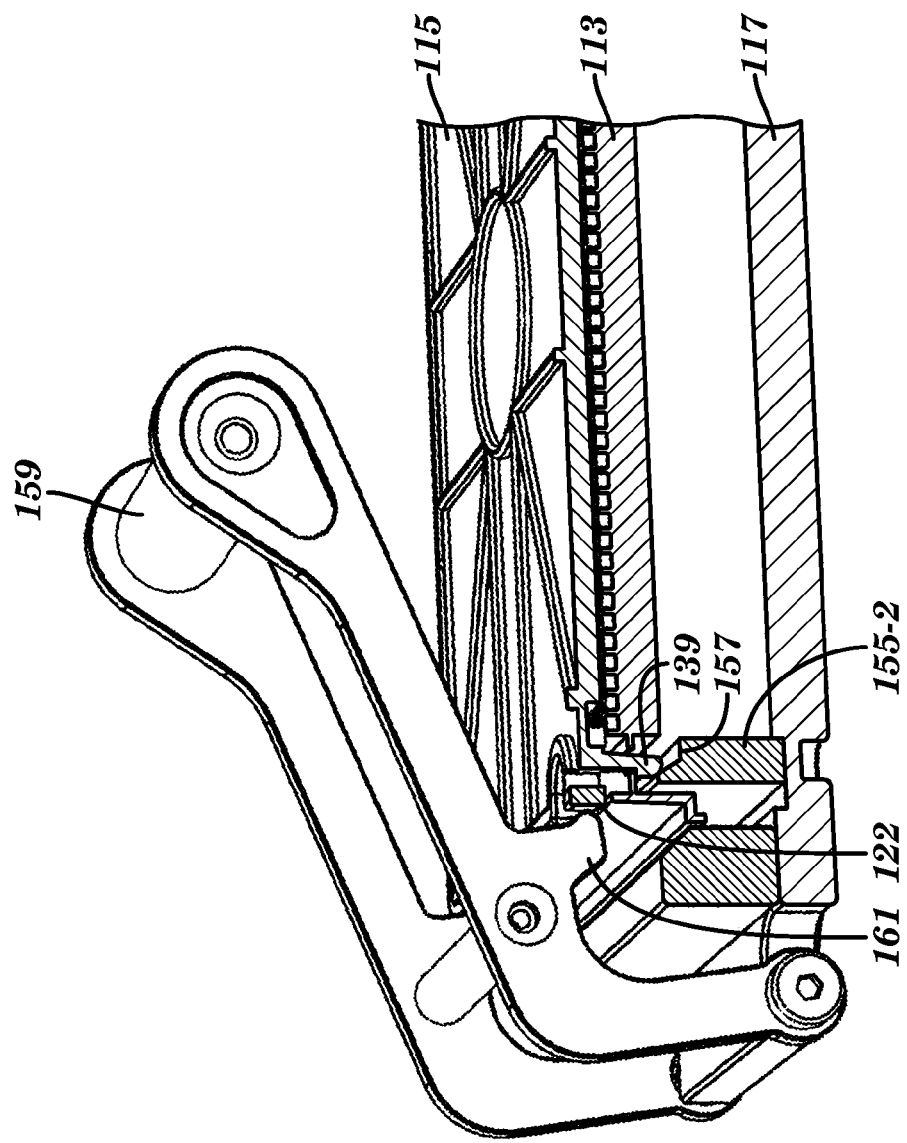
Figure 13C:
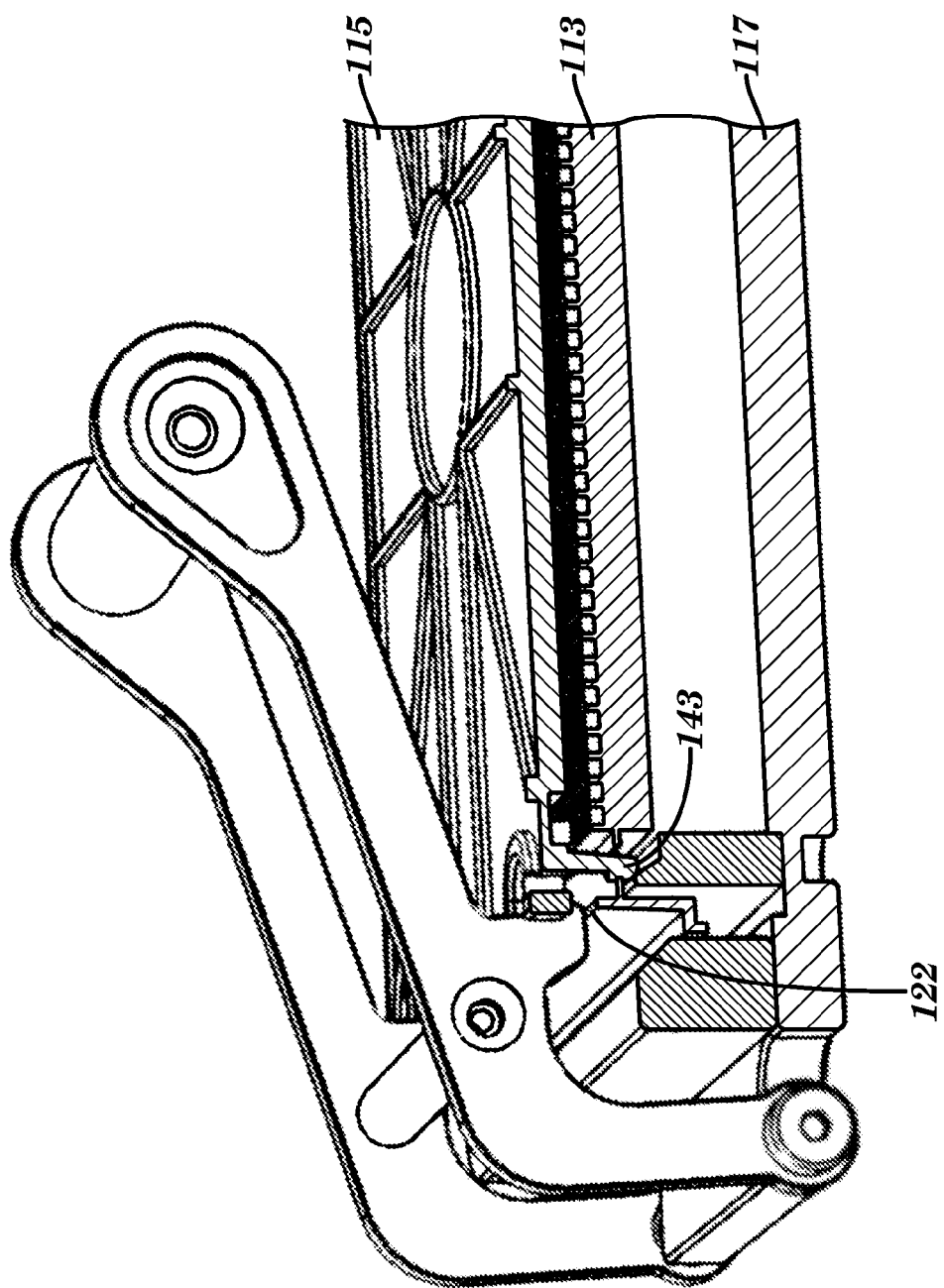
Figure 13D:
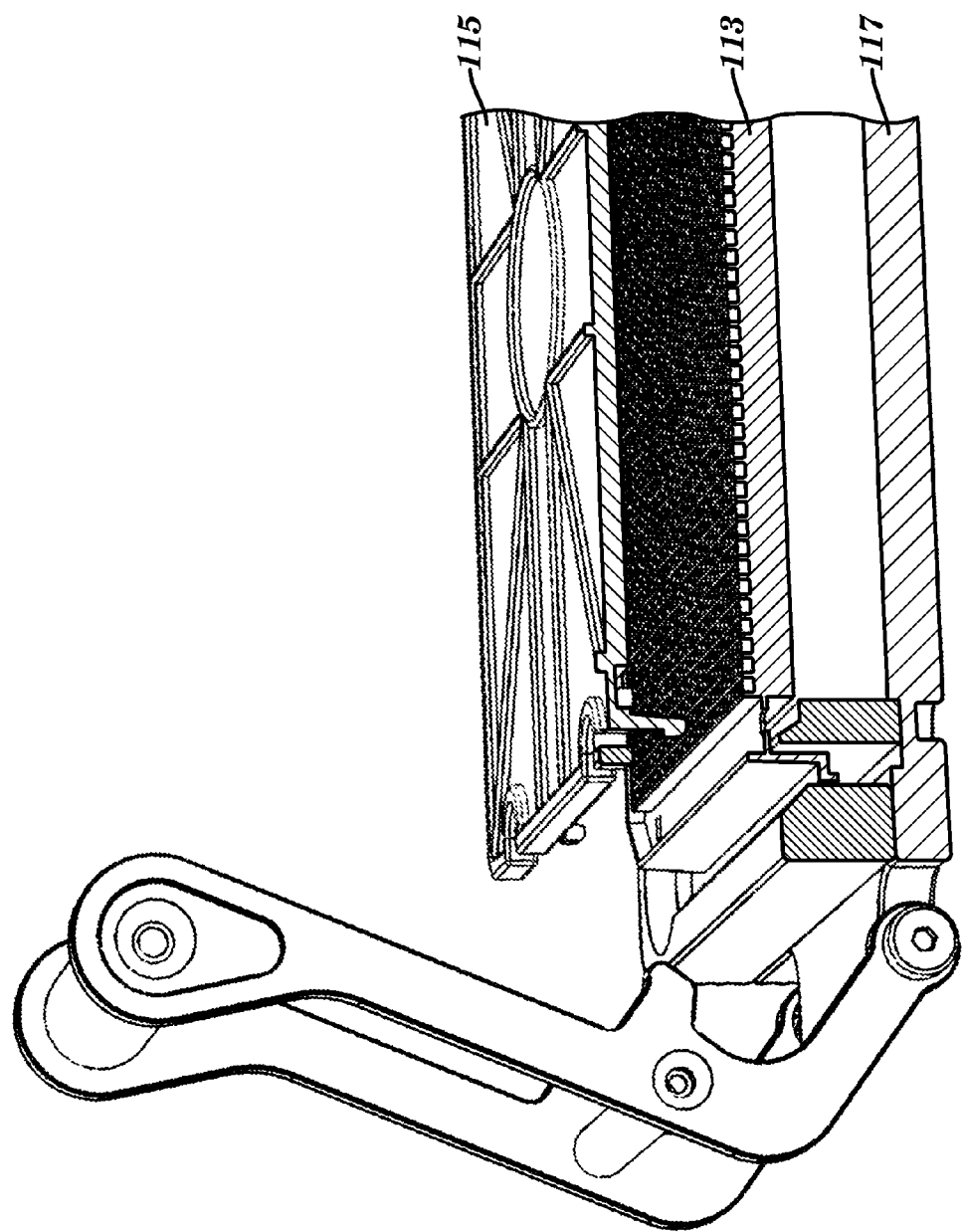

Aligned as such, microplate 113 is drawn down onto tool 117 until barb 143 of each latch 139 rests directly upon a support member 155. With microplate 113 supported by tool 117, handles 159 are pivoted inward (either manually or automatically) until fingers 161 abut against a thin outer wall 122 on microplate 113 that protrudes vertically up from the periphery of top surface 123, as shown in FIG. 13(b). At this time, further pivotal displacement of handles 159 inward urges microplate 113 downward onto tool 117. This downward force causes enlarged barb 143 of each latch 139 to ride inwardly along tapered surface 157 of a support member 155 which in turn causes latches 139 to deflect (i.e., articulate) inward to the extent necessary that latches 139 disengage from the underside of top surface 123. This disengagement causes barb 143 of each latch 139 to withdraw from its associated hole 129 in microplate 113 and thereby release lid 115 from microplate 113, as shown in FIG. 13(c). Disengaged lid 115 can then be fully separated from microplate 113 using either manual or automated means, as shown in FIG. 13(d).

Referring now to FIGS. 14a-17c, an automated lidder and/or delidder 200 (exterior view shown in FIG. 14a, cut-away view shown in FIG. 14b) is provided to automatically lid and delid microplate 13 and lid 15, as an alternative to the manual lidding/delidding process using tools 17, 117 described herein. Automated lidder and/or delidder 200 disclosed herein is discussed in connection with microplate 113 and lid 115, as shown in FIGS. 8-13(c), but it is understood that lidder/delidder 200 can also be used in connection with microplate 13 and lid 15, as shown in FIGS. 1-7(d).

Figure 14A:
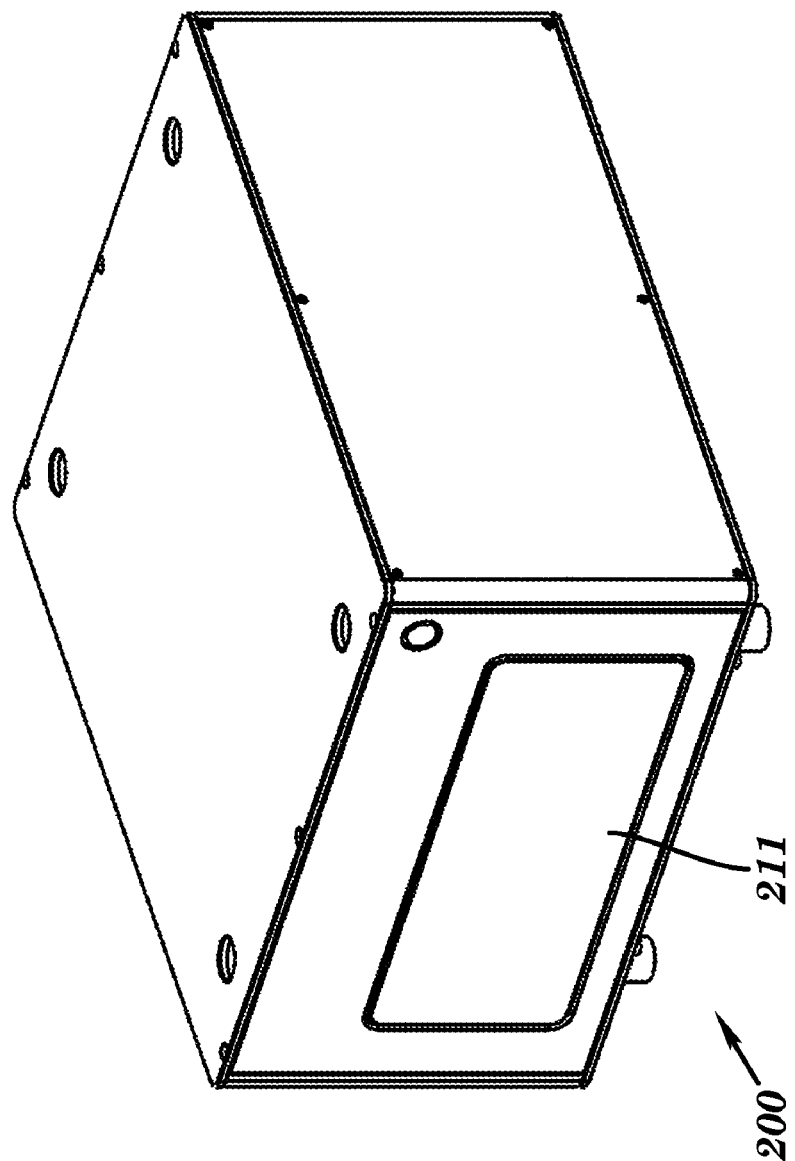
FIGS. 14A, 14B and 15A are top perspective views of an automated lidder/delidder for a microplate according to an embodiment of the invention.
Figure 14B:
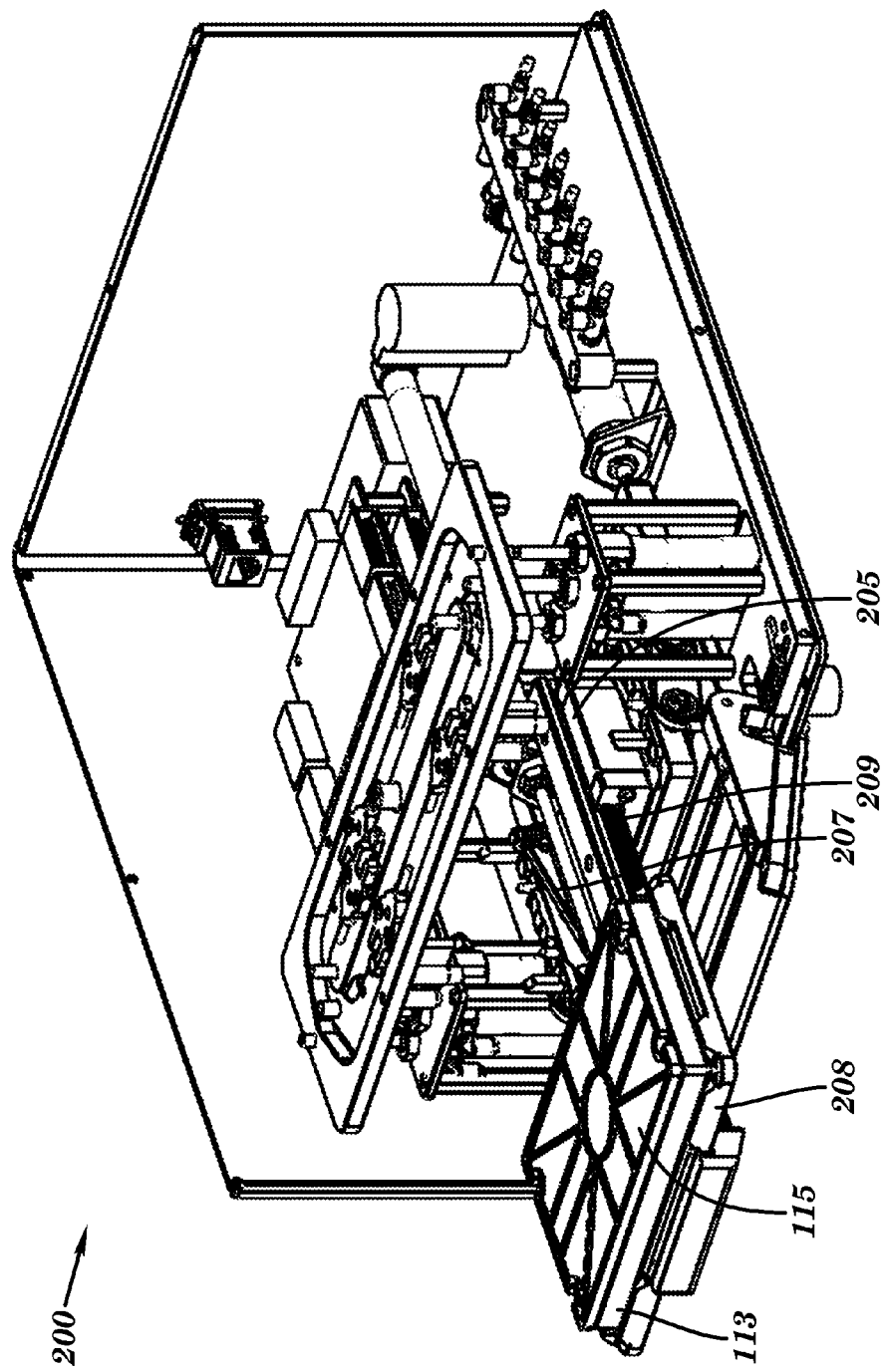
Figure 15A:
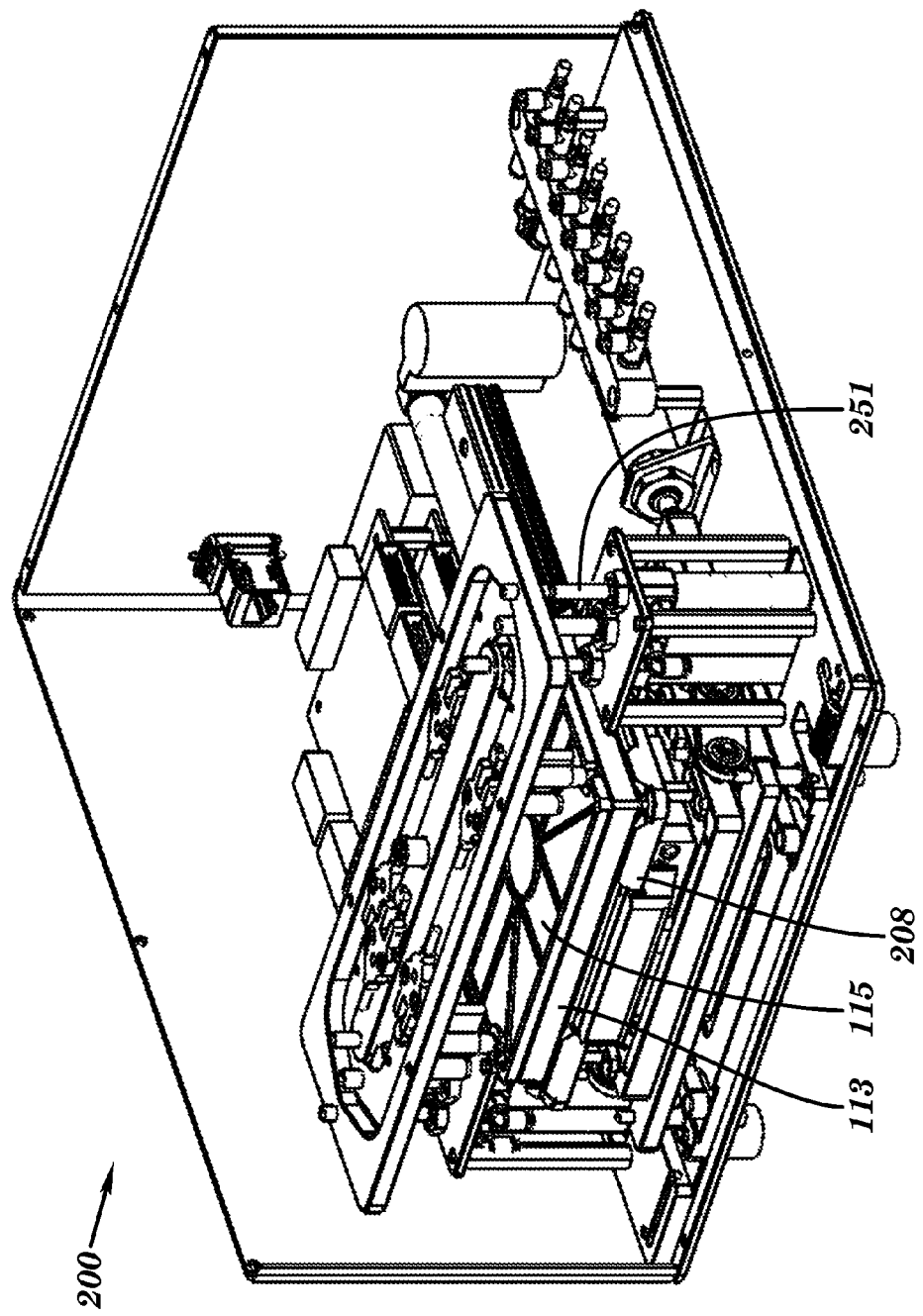
Figure 15B:
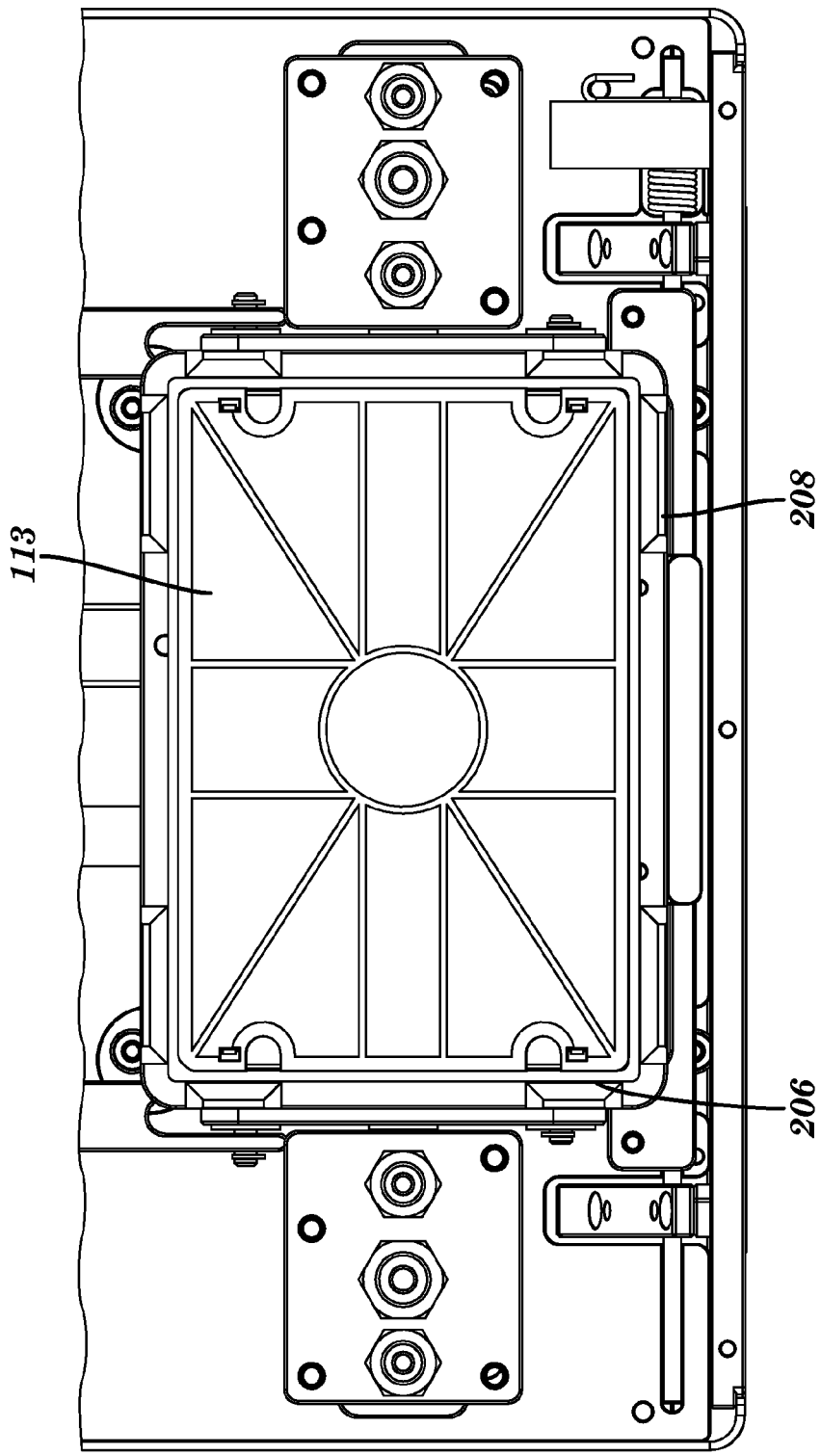
FIG. 15B is a top view of an automated lidder/delidder for a microplate according to an embodiment of the invention.

As shown in cut-away drawings FIGS. 14b and 15a, and top view drawing FIG. 15b, lidder/delidder 200 includes at least one platform 208 configured to hold a microplate, i.e., plate nest (FIG. 15a), that is configured to extend and retract, in and out of lidder/delidder 200. In other words, platform 208 is configured such that it moves between a first, exterior, position where it can load/unload microplates (FIG. 14b), and a second, interior, position, where the microplates can be lidded/delidded (FIG. 15a), as discussed in more detail herein. Platform 208 is configured such that it can receive microplate 113 from an operator or a robotic transfer mechanism (not shown), and 'trap' microplate 113 on a top surface of platform 208. Platform 208 can 'trap' microplate 113 using any known or later developed system of securing microplate 113, for example, by using one or more tabs 206 as shown in FIG. 15b. For example, platform 208 can be generally rectangularly shaped, with dimensions similar to microplate 113, and can include at least one tab 206 to lock, or trap, microplate 113 into place.

As shown in FIG. 14b, in the first, exterior, position, platform 208 is extended, and a lidded microplate 113 (i.e., microplate 113 with lid 115 attached), is placed on platform 208. Platform 208 is then retracted into the second, interior, position, within automated lidder/delidder 200, as shown in FIGS. 14a and 15a. Movement of platform 208 between these two positions can be achieved by actuating at least one piston cylinder 207 which guides platform 208 on at least one rail 209 in a bearing block 205. Turning back to FIG. 14a, automatic lidder/delidder 200 can further include an opening 201 that allows platform 208 to enter and exit lidder/delidder 200. Opening 201 can comprise any now known or later developed mechanism to allow platform 208 to enter/exit, such as, but not limited to, a door or window. Opening 201 can be configured to automatically open and shut, or can be manually opened or shut, or manually removed and/or replaced.

Figure 16A:
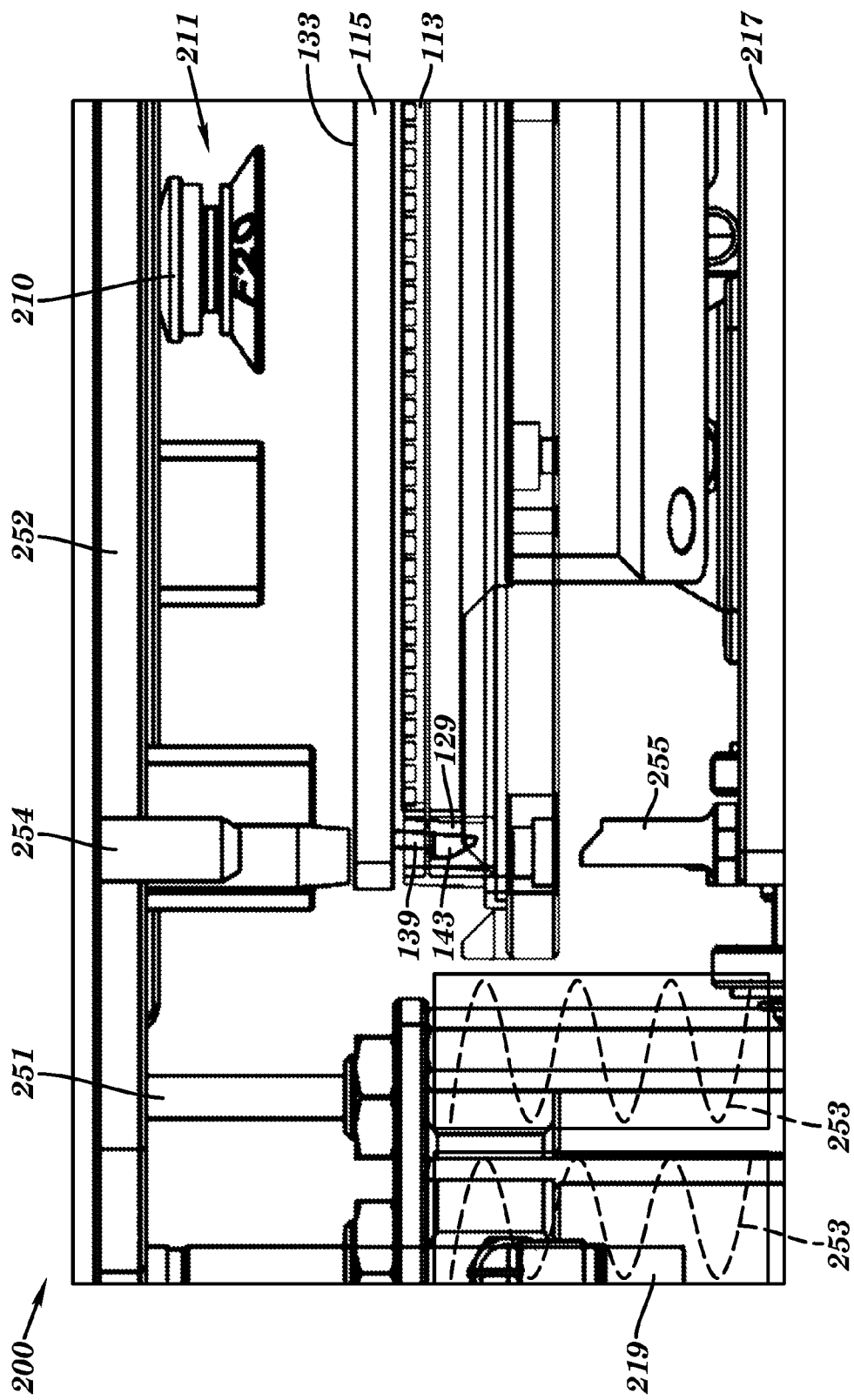
FIGS. 16A-16D are cross-sectional views of the automated lidder/delidder during the delidding process, according to an embodiment of the invention.
Figure 16B:
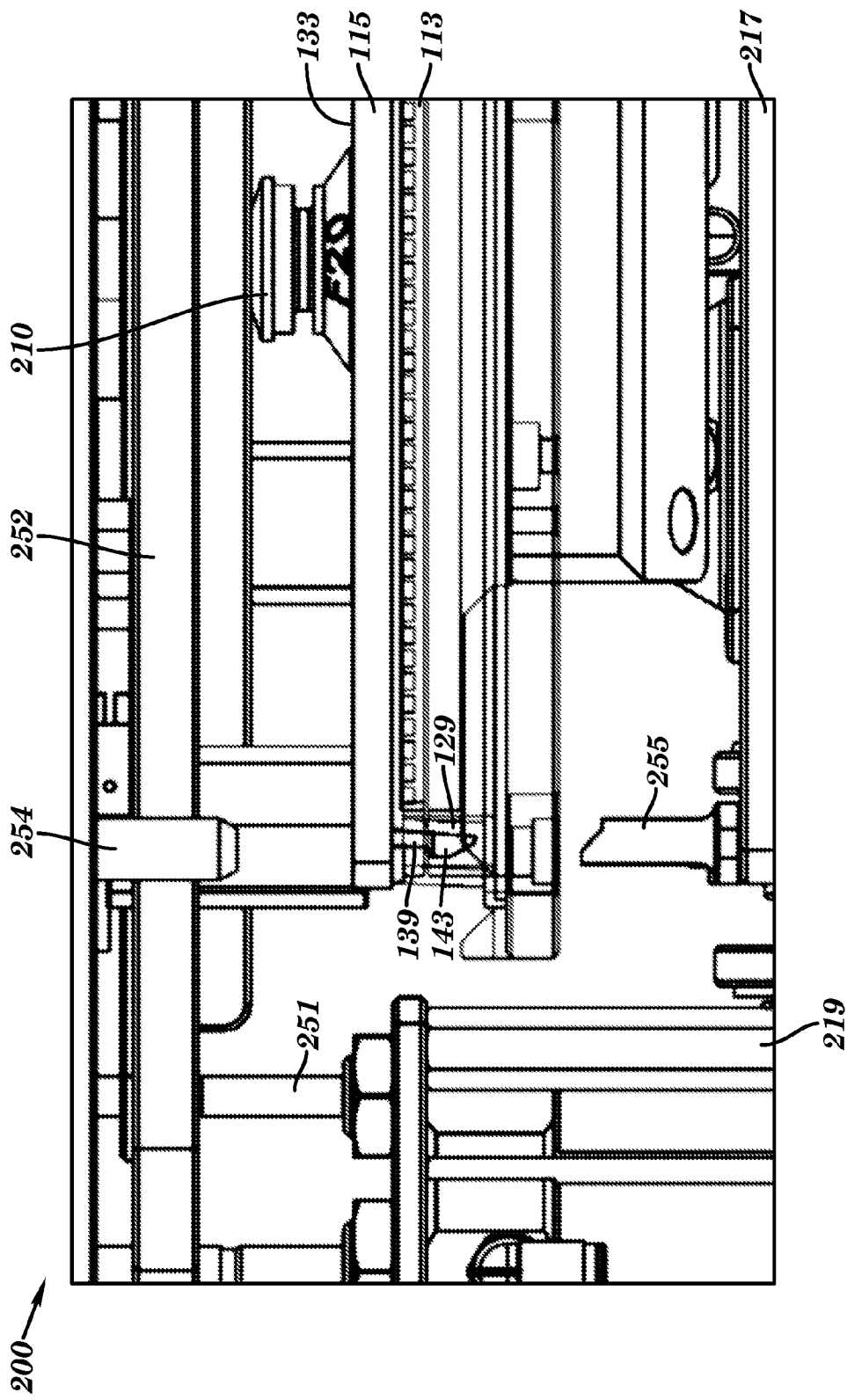

Operation of automatic lidder/delidder 200 to delid lidded microplate 113 is best described in connection with FIGS. 16a-16d. Turning to FIG. 16a, a cross-sectional view of lidder/delidder 200 with platform 208 retracted into the interior position is shown. As shown in FIG. 16a, automated lidder/delidder 200 further includes a lidding assembly 252 (also referred to as lid press assembly 252) positioned above platform 208, including a coupling device 211, for example, at least one vacuum cup 210, configured to adhere to lid 15. Vacuum cup 210 can be connected to a vacuum (not shown) using any known means. For example, polyurethane tubing can be used to connect the suction cup to a vacuum ejector, with a solenoid valve included in line with the vacuum ejector to control the vacuum. Vacuum cup 210 can comprise any suitable type of vacuum cup, including but not limited to a flat vacuum cup, a bellows type vacuum cup (either single bellows or multiple bellows), or deep cups. Vacuum cup 210 can also be any desired shape and size. While a vacuum cup 210 is discussed herein, it is understood that any suitable coupling device 211 can be used to couple lid 115 to lid press assembly 252. For example, coupling device 211 could include mechanical means of gripping lid 115, such as hooks, prongs, pivotable jaws, clamps, grippers or the like, while lid 115 could be adapted to receive these mechanical means such that lid 115 would be mechanically coupled to lid press assembly 252.

Lid press assembly 252 may further include at least one member 254 which is configured to press down on lid 115. Member 254 is shown in FIGS. 16a-16d as a plurality of members 254, each extending substantially orthogonally from of lid press assembly 252, but it is understood that other configurations of member(s) can also be used to press down on lid 115. Lid press assembly 252, via vacuum cup 210 and members 254, can be moved by at least one piston cylinder 251 and an internal spring 253 (FIG. 16a) inside piston cylinder 251, as understood by one of skill in the art. It is also understood that any known or later developed means of moving lid press assembly can be used, such as pneumatic, hydraulic or mechanical means, for example, including but not limited to pneumatic cylinders, mechanical actuators such as a hydraulic cylinders, and mechanical elements such as grippers or clamps. In addition, as known in the art, a spring mechanism can be used in connection with a piston cylinder if desired, for example, an internal spring 253, shown in phantom in FIG. 16a.

Figure 16C:
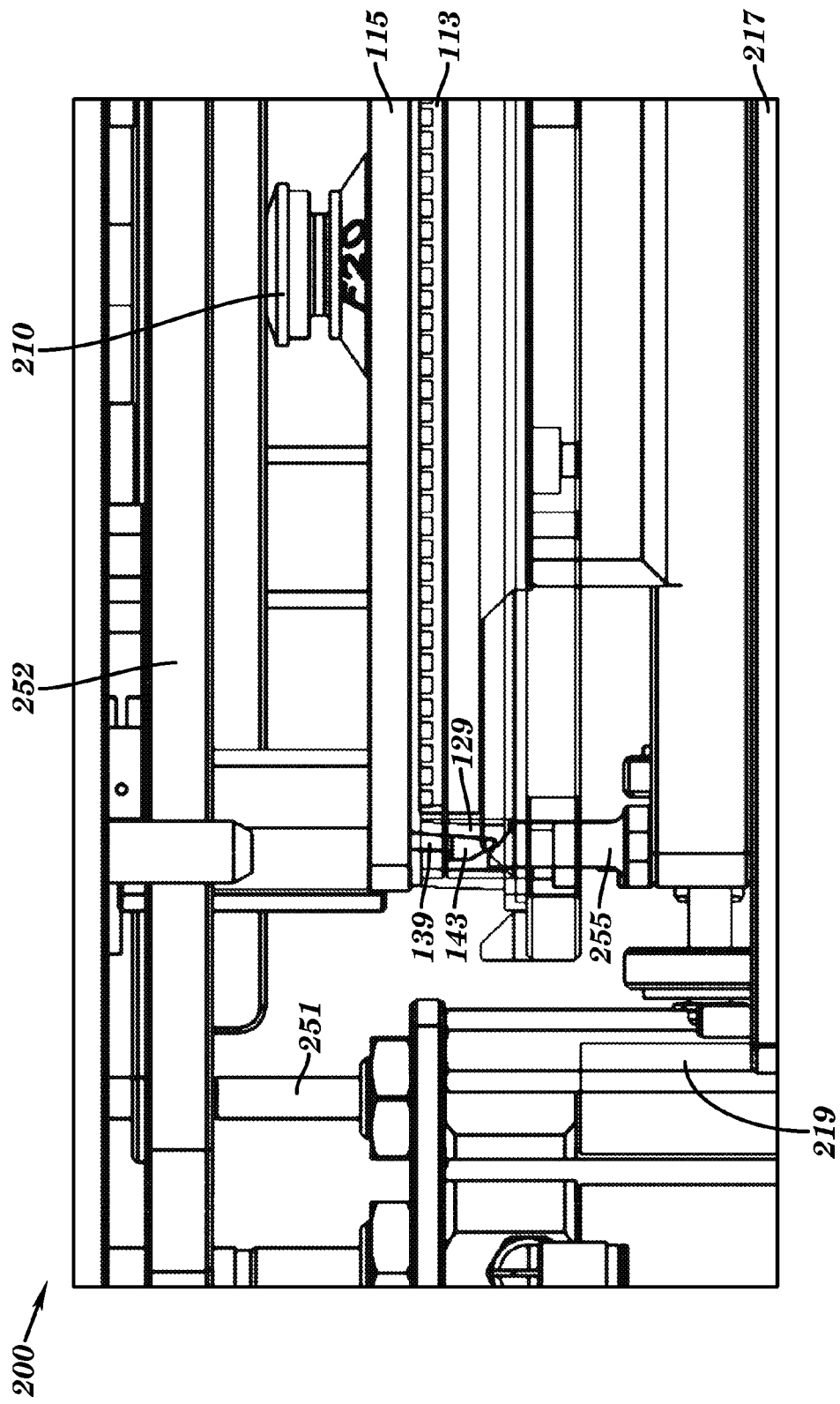
Figure 16D:
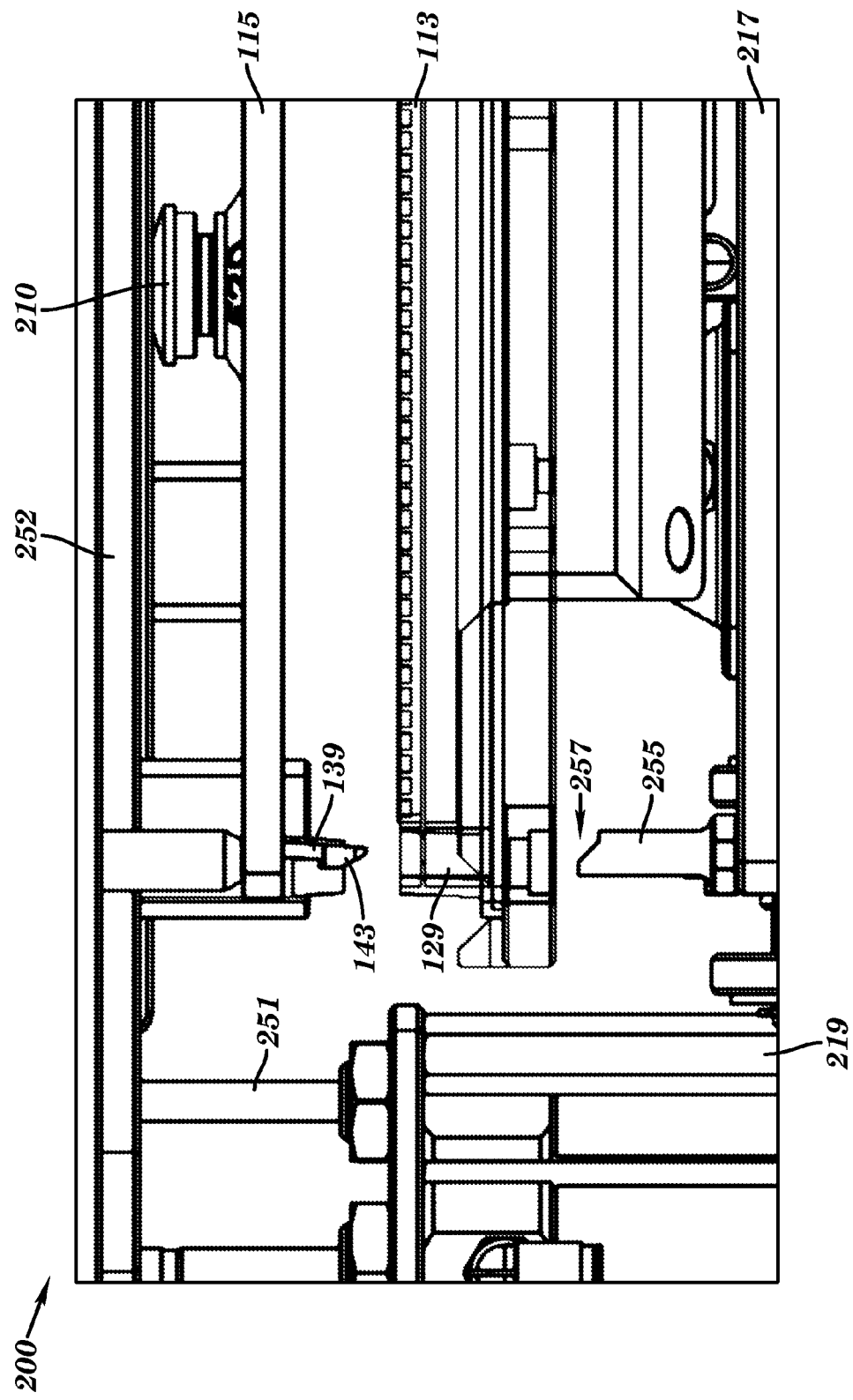

Lid press assembly 252 is configured to move between a lidding/delidding position proximate to microplate 113 (FIGS. 16b and 16c), and a neutral position away from microplate 113 (FIGS. 16a and 16d). For example, coupling device 211 is positioned such that once platform 208 (and lidded microplate 113) is retracted into the interior position, lidded microplate 113 is substantially centered below coupling device 211, e.g., vacuum cup 210. Once microplate 113 with lid 115 is in the interior position, lid press assembly 252 is moved from its neutral position (FIG. 16a) and lowered into the lidding/delidding position (FIG. 16b), with coupling device 211, and members 254, contacting a substantially flat top surface 133 of lid 115. (This movement of lid press assembly 252 is also discussed herein in connection with the lidding process and shown in FIGS. 17a-17c). Lid press assembly 252 can be moved by two actuated piston cylinders 251, as shown in FIGS. 15a and 16a-16d. Coupling device 211 can then be actuated, such that it will couple lid 115, for example, the vacuum connected to vacuum cup 210 can be turned on, causing vacuum cup 210 to adhere to lid 115.

As shown in FIGS. 16a-16d, automated lidder/delidder 200 further includes a base 217 positioned below platform 208. Base 217 may have at least one delidding post 255 projecting substantially orthogonally towards microplate 113. Each delidding post 255 is coaxially aligned with a corresponding hole 129 in microplate 113. Base 217 is configured to move between a neutral position away from microplate 113 (FIGS. 16a and 16b) and a delidding position proximate to microplate 113 (FIG. 16c). For example, in order to delid lidded microplate 113, base 217 may be automatically moved by at least one piston cylinder 219 and internal spring 253 (FIG. 16a) inside piston cylinder 219, as understood by one of skill in the art, from neutral position shown in FIG. 16a, into the delidding position, as shown in FIG. 16c. In the delidding position, each delidding post 255 of base 217 is configured to extend into a corresponding hole 129 in microplate 113 to engage a corresponding projection 139 extending substantially orthogonally from lid 115 into hole 129.

As shown in FIG. 16c, each delidding post 255 is configured to engage a corresponding projection 139 such that it releases projection 139 from hole 129, thus releasing lid 115 from microplate 113. In one embodiment, each delidding post 255 can include a taper 257 that is configured to contact a barb 143 of latch 139 in order to disengage barb 143 from microplate 113, similar to support members 155 that assist in the manual delidding process with tool 117. As shown in FIGS. 16c and 16d, once projection 139, and therefore lid 115, is disengaged from microplate 113 (FIG. 16c), lid press assembly 252, via coupling device 211, e.g., vacuum cup 210, may automatically lift lid 115 away from microplate 113, as lid press assembly 252 moves into its neutral position (FIG. 16d). Lid press assembly 252 can then be retracted upwards, away from microplate 113. In one embodiment where air pistons 251 are used, lid press assembly 252 can be retracted by turning off the air to the piston cylinders 251. Cylinders 251 can then return to their neutral position via internal springs 253 (FIG. 16a). Optionally, an optical sensor (not shown) can be used to determine whether lid 115 has actually adhered to coupling device 211, e.g., vacuum cup 210. Base 217 may also then be lowered into its neutral position (FIG. 16d), away from microplate 113. Cylinders 219 can then return to their neutral position via springs 253 (FIG. 16a).

Platform 208 can then be extended to remove microplate 113, now delidded, from lidder/delidder 200. As shown in FIG. 14b, platform 208 can be moved by actuating the at least one piston cylinder 207 which guides platform 208 on at least one rail 209 in a bearing block 205.

Figure 17A:
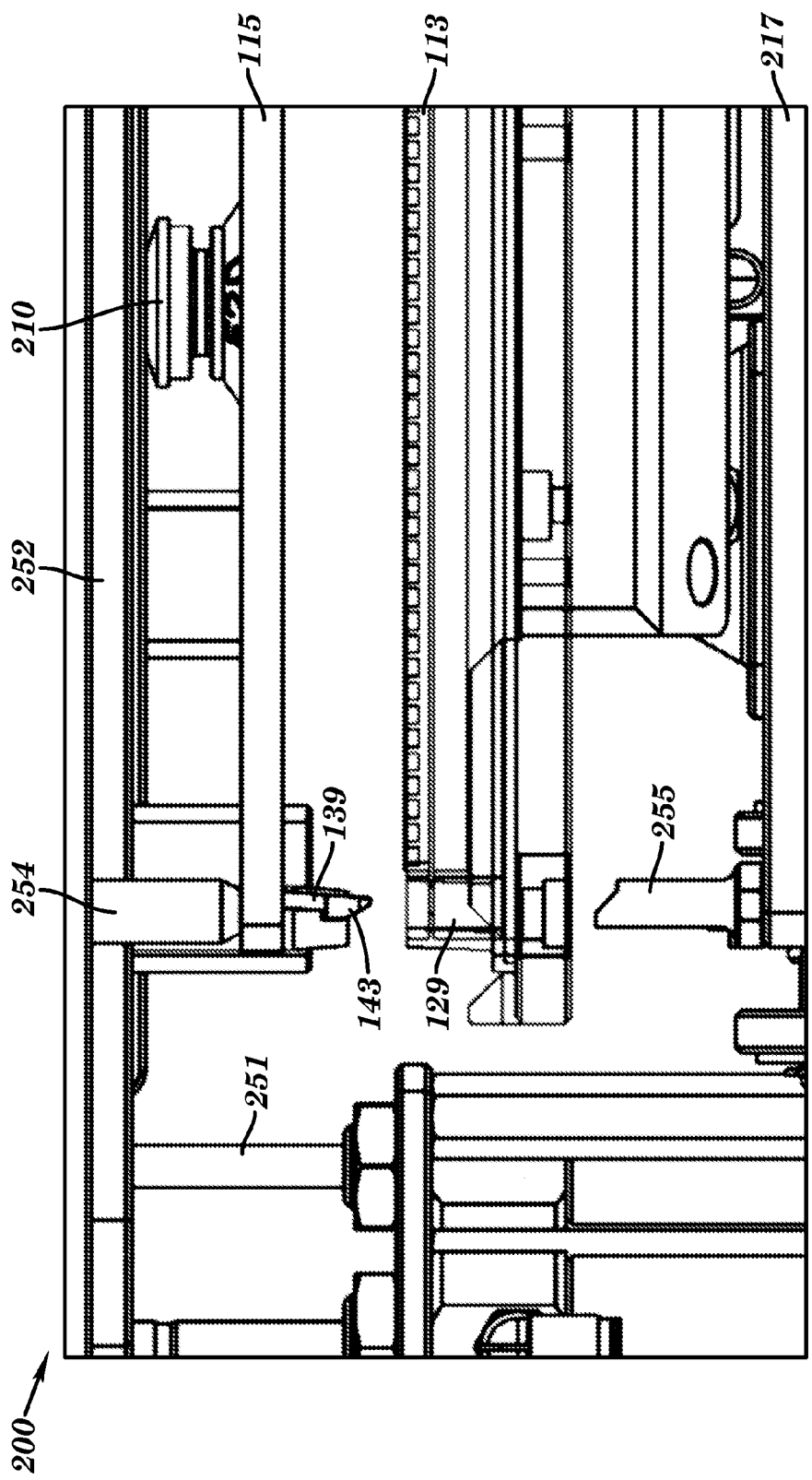
FIGS. 17A-17C are cross-sectional views of the automated lidder/delidder during the lidding process, according to an embodiment of the invention.
Figure 17B:
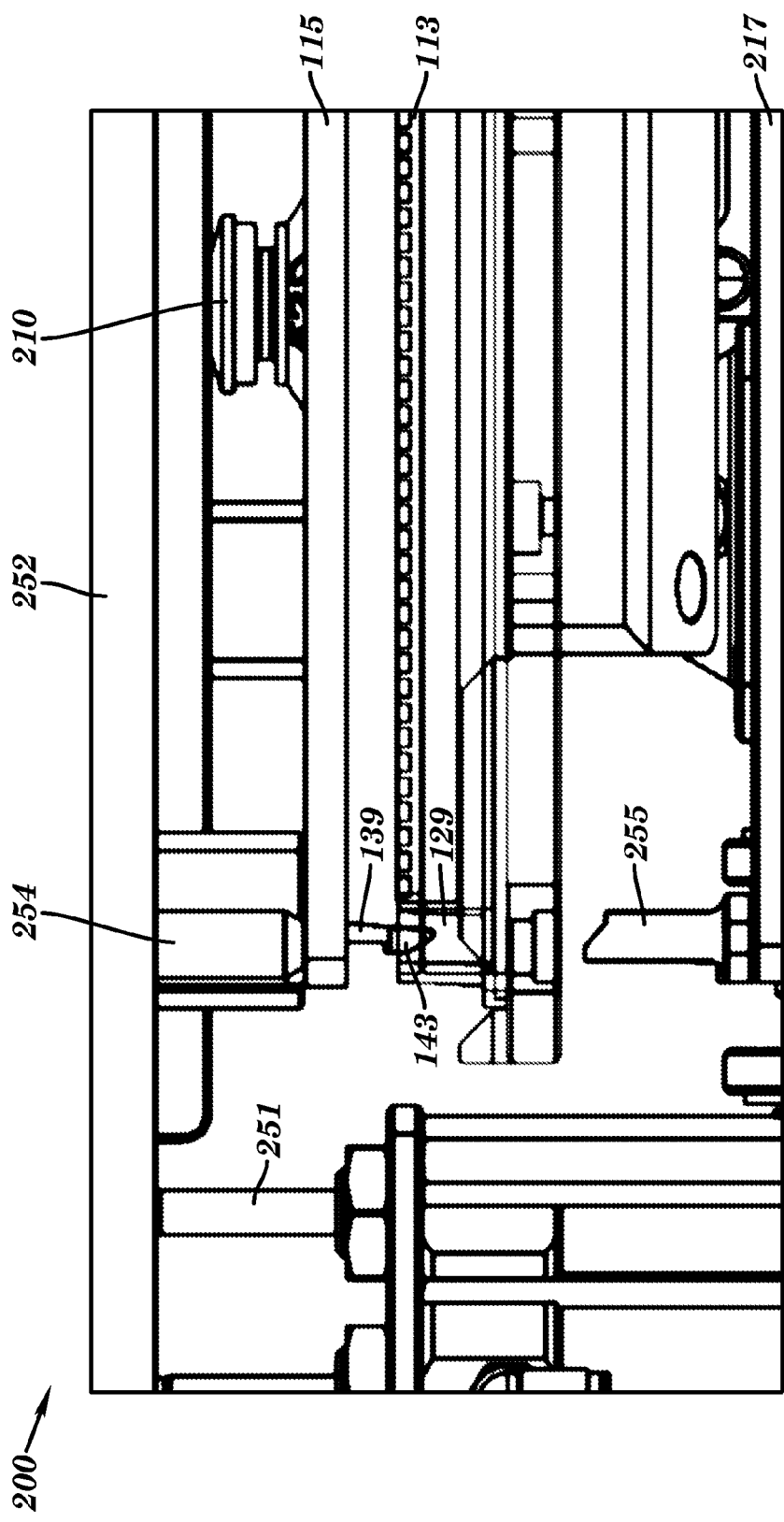
Figure 17C:
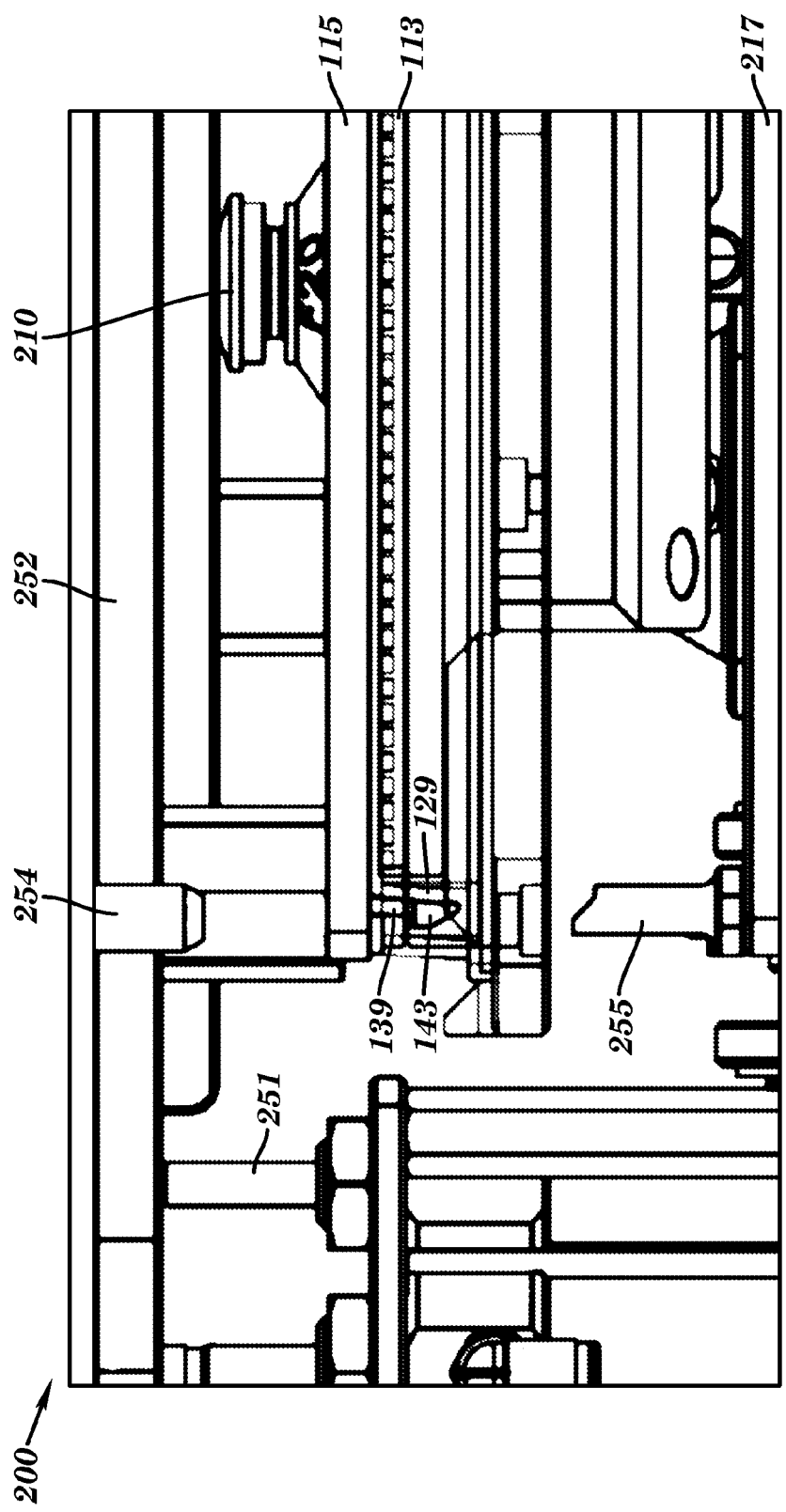

Turning to FIGS. 17a-17c, an automated lidding process is shown, with platform 208 retracted into the second, interior, position within lidder/delidder 200, bringing an unlidded microplate 113 within lidder/delidder 200. As shown in FIG. 17a, a lid 115 is attached to coupling device 211, e.g., vacuum cup 210, of lid press assembly 252 (for example, from a delidding process as described herein), and is suspended above the unlidded microplate 113. As discussed herein, lid 115 includes at least one projection 139 projecting substantially orthogonally downward towards microplate 113. Each projection 139 is dimensioned to project at least partially through a corresponding hole 129 in microplate 113 in response to lid 115 being mounted on microplate 113, as discussed herein.

As also discussed herein, lid press assembly 252 moves lid 115 from its neutral position away from microplate 113 (FIG. 17a) into its delidding/lidding position proximate to microplate 113 (FIG. 17b), for example, via actuated piston cylinders 251. As shown in FIG. 17b, in the lidding position, lid press assembly 252, via vacuum cup 210 and members 254, act to press down on lid 115 such that each projection 139 of lid 115 engages a corresponding hole 129 in microplate 113. As discussed herein in connection with the manual lidding process using tool 117, projection 139 can comprise a latch. In one embodiment, latch 139 can comprise a single deflectable arm 139 including an outwardly extending barb 143 formed on a free end thereof, and in another embodiment, latch 139 can include a compressible arrowhead having a pair of legs spaced apart from one another to define a narrow slot therebetween, a free end of each leg including an outwardly extending barb 143.

In either configuration of projection 139, as shown in FIG. 17c, each barb 143 can snap into a corresponding hole 129 and latch against the underside of top surface 123 (FIG. 12c) of microplate 113. After lid 115 is secured to microplate 113, coupling device 211, e.g., vacuum cup 210, may release lid 115, for example, by turning off the vacuum connected to vacuum cup 210, or releasing a mechanical means such as a gripper. An optical sensor (not shown) can be configured to detect flags (not shown) on each corner of lid 115 to determine if lid 115 is pressed flat onto microplate 113 and is no longer attached to coupling device 210. As shown in FIG. 17c, once lid 115 is no longer adhered to coupling device 210, lid press assembly 252, including coupling device 210, may move into its neutral position, automatically moving away from lid 115 and microplate 113. This movement can occur, for example, by turning off air to piston cylinders 251. The cylinders can then return to their neutral position via internal springs 25 (FIG. 16a). Platform 208 can then be extended to remove lidded microplate 113 from lidder/delidder 200. Platform 208 can be moved by actuating the at least one piston cylinder 207 which guides platform 208 on at least one rail 209 in a bearing block 205.

While piston cylinders and springs have been discussed herein to describe the movement of the various elements disclosed herein in connection with lidder/delidder 200, it is understood that other known means of moving these elements relative to each other is also disclosed. For example, pneumatic, hydraulic or mechanical means can be used, for example, including but not limited to pneumatic cylinders, mechanical actuators such as a hydraulic cylinders, and mechanical elements such as grippers or clamps. It is also understood that when springs are discussed herein in connection with piston cylinders, one example of springs 253 positioned inside a cylinder is shown in FIG. 16a.

The embodiments shown in the present invention are intended to be merely exemplary and those skilled in the art shall be able to make numerous variations and modifications without departing from the spirit of the present invention. All such variations and modifications are intended to be within the scope of the present invention as defined in the appended claims.

We claim:

1. An apparatus for lidding or delidding a microplate, the apparatus comprising:
   a platform configured to hold a microplate, wherein the microplate comprises
      a sample area shaped to define a plurality of individual wells, and
      an outer frame surrounding the sample area, wherein the outer frame includes at least one opening;
   a lidding assembly positioned above the platform, the lidding assembly including a coupling device configured to couple the lidding assembly to a lid for the microplate, wherein the lidding assembly is configured to move the lid between a first position proximate to the microplate and a second position away from the microplate, wherein the lid includes at least one projection projecting substantially orthogonally towards the microplate, the at least one projection dimensioned to project at least partially through the at least one opening in the outer frame of the microplate in response to the lid being mounted on the microplate in the first position; and
   a base positioned below the platform, the base having at least one delidding post projecting substantially orthogonally towards the microplate, wherein the base is configured to move between a third position proximate to the microplate and a fourth position away from the microplate, wherein the at least one delidding post is configured to extend into the at least one opening in the outer frame of the microplate to engage and release the at least one projection from the microplate in response to the base being in the third position.

2. The apparatus of claim 1, wherein the at least one projection is adapted to matingly engage the microplate upon insertion through the opening in response to the lid being in the first position.

3. The apparatus of claim 1, wherein the outer frame includes a top surface shaped to include the at least one opening and a substantially open bottom surface, the at least one opening in the top surface being accessible through the open bottom surface.

4. The apparatus of claim 1, wherein the lid comprises a substantially rectangular plate having a top surface and a bottom surface.

5. The apparatus of claim 4, wherein the at least one projection includes a latch which protrudes substantially orthogonally from the bottom surface of the lid.

6. The apparatus of claim 5, wherein the latch includes a compressible arrowhead having a pair of legs spaced apart from one another to define a narrow slot therebetween, a free end of each leg including an outwardly extending barb.

7. The apparatus of claim 5, wherein the latch includes a single deflectable arm with an outwardly extending barb formed on a free end thereof.

8. The apparatus of claim 4, wherein the lid further comprises a gasket affixed to the plate, the gasket protruding beyond the bottom surface of the plate.

9. The apparatus of claim 1, wherein a free end of the at least one delidding post includes a taper.

10. The apparatus of claim 1, wherein the at least one delidding post deflects a corresponding projection of the lid in response to the base being in the third position to disengage the at least one projection from the microplate.

11. The apparatus of claim 1, wherein the platform is configured to move between an exterior position outside the apparatus and an interior position within the apparatus.

12. The apparatus of claim 1, wherein the coupling device comprises at least one vacuum cup.

* * * * *